(12) United States Patent
Park et al.

(10) Patent No.: US 12,290,406 B2
(45) Date of Patent: May 6, 2025

(54) ULTRASOUND DIAGNOSTIC APPARATUS AND METHOD FOR OPERATING SAME

(71) Applicant: SAMSUNG MEDISON CO., LTD., Gangwon-do (KR)

(72) Inventors: Moonho Park, Seoul (KR); Kihong Son, Seoul (KR); Hojun Lee, Seoul (KR); Anjan Kumar Paul, Seoul (KR); Sujin Ahn, Seoul (KR); Yeongkyeong Seong, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 230 days.

(21) Appl. No.: 17/908,445

(22) PCT Filed: Dec. 16, 2020

(86) PCT No.: PCT/KR2020/018470
§ 371 (c)(1),
(2) Date: Aug. 31, 2022

(87) PCT Pub. No.: WO2021/194053
PCT Pub. Date: Sep. 30, 2021

(65) Prior Publication Data
US 2024/0023939 A1 Jan. 25, 2024

(30) Foreign Application Priority Data
Mar. 27, 2020 (KR) .................. 10-2020-0037792

(51) Int. Cl.
*A61B 8/08* (2006.01)
*A61B 8/00* (2006.01)
*G06T 7/00* (2017.01)

(52) U.S. Cl.
CPC ............ *A61B 8/5223* (2013.01); *A61B 8/085* (2013.01); *A61B 8/4405* (2013.01); *A61B 8/463* (2013.01);
(Continued)

(58) Field of Classification Search
CPC ... A61B 5/4041; A61B 5/4047; A61B 5/4052; A61B 2018/00434; A61B 2090/378;
(Continued)

(56) References Cited

U.S. PATENT DOCUMENTS

| 8,137,274 B2 | 3/2012 | Weng et al. |
| 2006/0184022 A1 | 8/2006 | Johnson |

(Continued)

FOREIGN PATENT DOCUMENTS

| CN | 102324094 A | 1/2012 |
| CN | 105232081 A | 1/2016 |

(Continued)

OTHER PUBLICATIONS

International Search Report dated Mar. 26, 2021 issued in International Patent Application No. PCT/KR2020/018470 (with English translation).

(Continued)

*Primary Examiner* — Gerald Johnson
(74) *Attorney, Agent, or Firm* — Morgan, Lewis & Bockius LLP

(57) ABSTRACT

Disclosed is a method for operating an ultrasound diagnostic apparatus, comprising the steps of: acquiring a first ultrasound image of an object; detecting a first nerve region corresponding to a first target nerve in the first ultrasound image; determining whether an abnormal region is present in the first nerve region of the first ultrasound image, on the basis of a determination standard for determining whether a target nerve is abnormal; and on the basis of a result of (Continued)

determining whether an abnormal region is present in the first nerve region, displaying at least one of information on the abnormal region and basis information regarding the basis for determining the abnormal region as abnormal.

11 Claims, 18 Drawing Sheets

(52) U.S. Cl.
CPC .. *G06T 7/0014* (2013.01); *G06T 2207/10132* (2013.01); *G06T 2207/20081* (2013.01); *G06T 2207/20084* (2013.01)

(58) Field of Classification Search
CPC ................. A61B 5/4893; A61B 6/506; G06T 2207/20081; G06T 2207/10132
See application file for complete search history.

(56) References Cited

U.S. PATENT DOCUMENTS

| | | | |
|---|---|---|---|
| 2016/0000367 A1 | 1/2016 | Lyon | |
| 2017/0024883 A1 | 1/2017 | Urabe et al. | |
| 2018/0122074 A1* | 5/2018 | Li | A61B 5/7425 |
| 2018/0168539 A1* | 6/2018 | Singh | A61B 8/4483 |
| 2019/0311478 A1 | 10/2019 | Avendi et al. | |
| 2021/0327052 A1 | 10/2021 | Hafiane | |

FOREIGN PATENT DOCUMENTS

| | | |
|---|---|---|
| CN | 110574036 A | 12/2019 |
| JP | 2013-063259 A | 4/2013 |
| JP | 2017-023347 A | 2/2017 |
| JP | 2018-057428 A | 4/2018 |
| KR | 10-2015-0000261 A | 1/2015 |
| KR | 10-2016-0012758 A | 2/2016 |
| KR | 2018-057428 A | 4/2018 |
| WO | 2013/031216 A1 | 3/2013 |

OTHER PUBLICATIONS

Extended European Search Report issued Dec. 15, 2023 for European Patent Application No. 20926960.4.
Supplementary European Search Report issued Jan. 9, 2024 for European Patent Application No. 20926960.4.
Marharjan, et al., "Guided Ultrasound Imaging using a Deep Regression Network", 2020, SPIE, vol. 11319, p. 1-9, XP060129774.
Brattain, et al., "Machine learning for medical ultrasound: status, methods, and future opportunities", 2018, Abdominal Radiology, vol. 43, Issue No. 4, p. 786-799, XP036472474.
Korean Office Action dated Jan. 13, 2025 issued in Korean Patent Application No. 10-2020-0037792 (with English translation).
Chinese Office Action dated Feb. 26, 2025 issued in Chinese Patent Application No. 202080099165.2 (with English translation).

* cited by examiner

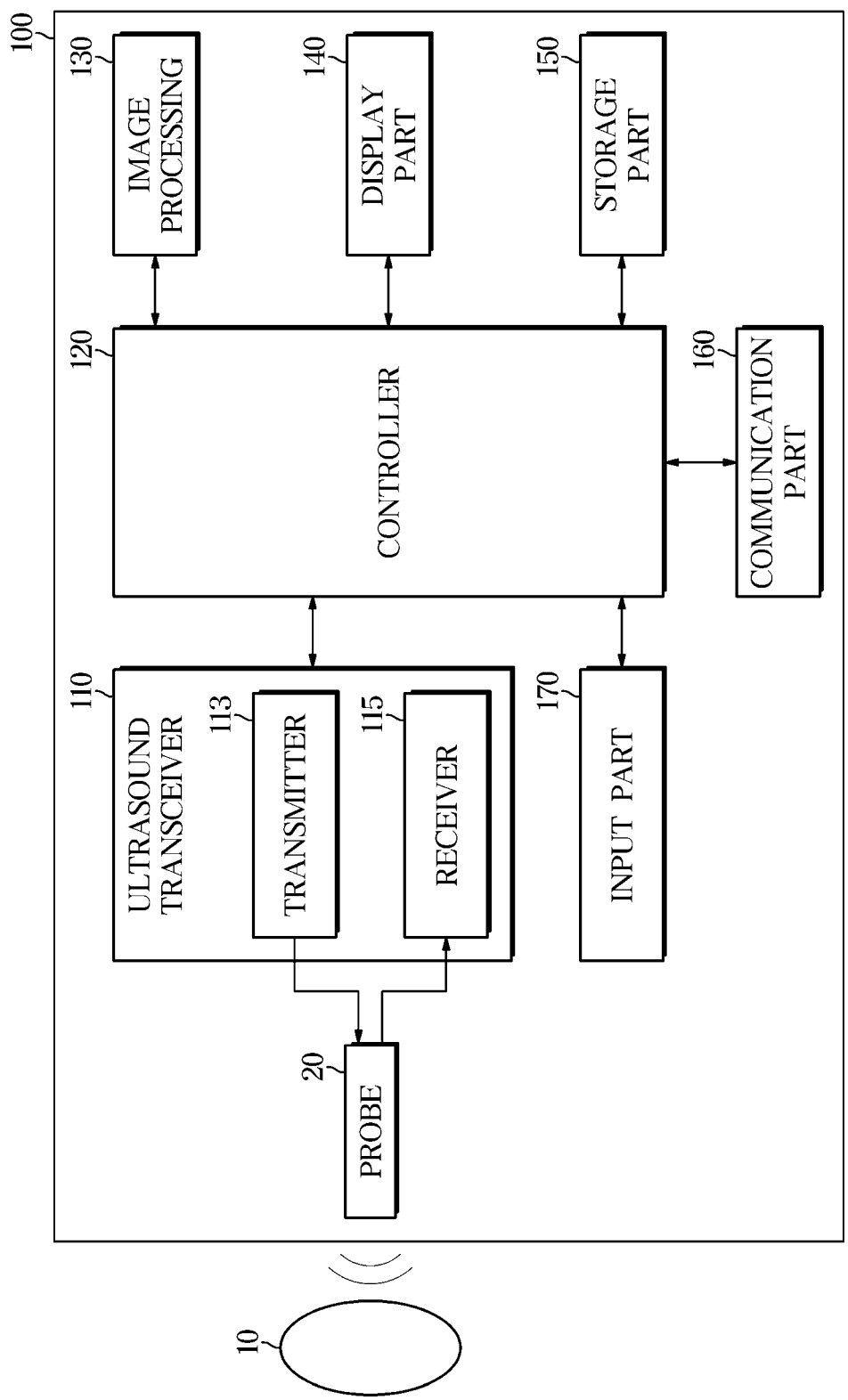

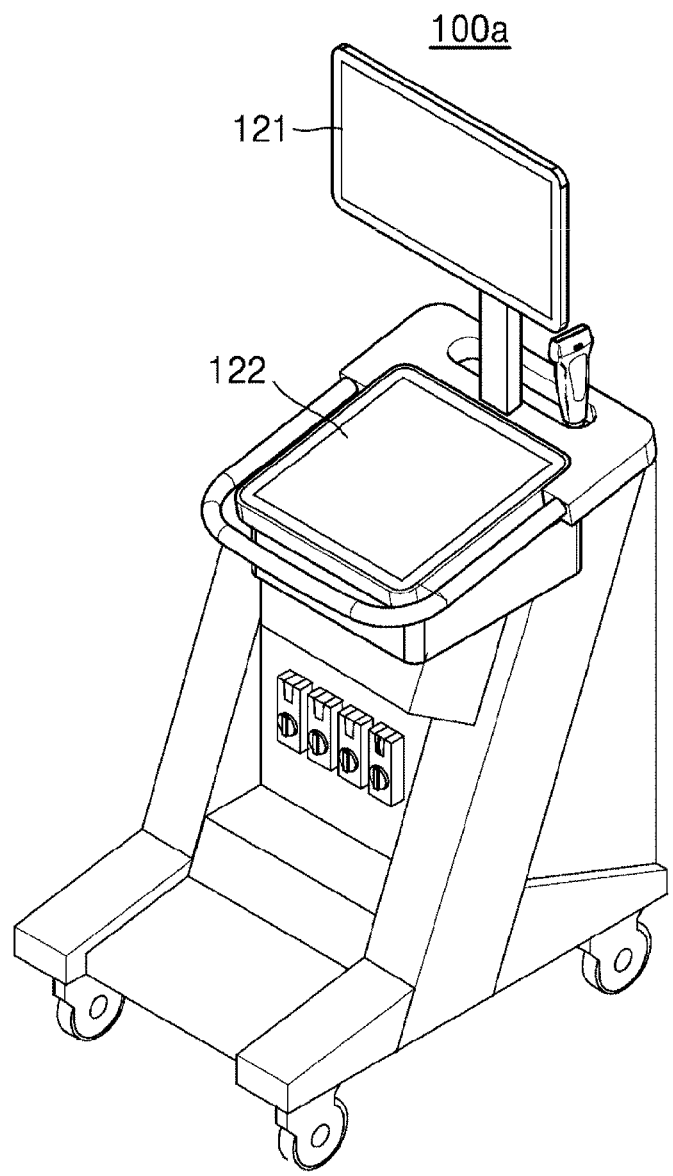

FIG. 9C
930
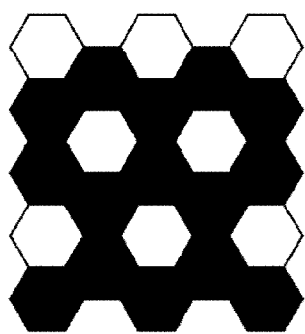
940
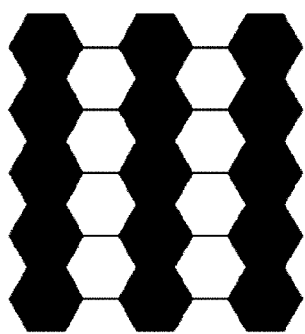
950
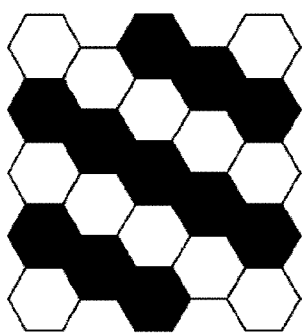
960
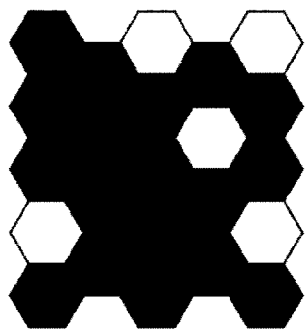
970
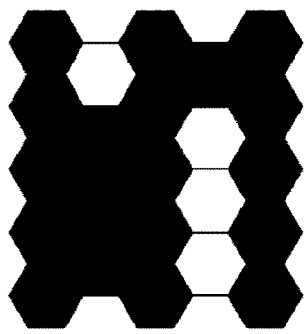
980
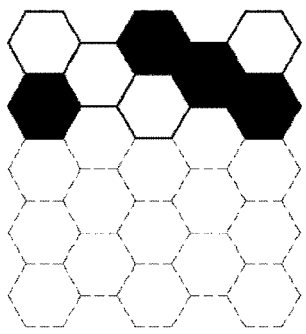

ULTRASOUND DIAGNOSTIC APPARATUS AND METHOD FOR OPERATING SAME

CROSS-REFERENCE OF RELATED APPLICATIONS

This application is the U.S. National Phase under 35 U.S.C. § 371 of International Patent Application No. PCT/KR2020/018470, filed on Dec. 16, 2020, which in turn claims the benefit of Korean Application No. 10-2020-0037792, filed on Mar. 27, 2020, the entire disclosures of which applications are incorporated by reference herein.

TECHNICAL FIELD

The present invention relates to an ultrasound diagnostic apparatus and a method for operating the same.

BACKGROUND ART

Ultrasound diagnostic apparatuses irradiate an ultrasound signal generated from a transducer of a probe onto an object and receive information about a signal reflected from the object, thereby obtaining at least one image of an internal part (e.g., soft tissue or blood flow) of the object.

DISCLOSURE

Technical Problem

The present invention is directed to determining whether an abnormality is present in a nerve region detected from an ultrasound image, and on the basis of the determination result, providing information about an abnormal region of the nerve region or basis information about a basis for determining the abnormal region.

The present invention is also directed to detecting a nerve region from an ultrasound image acquired in real time, and accurately providing information about whether a nerve is abnormal and basis information about a basis for determining the abnormality.

Technical Solution

According to one embodiment, there is provided a method for operating an ultrasound diagnostic apparatus, the method including acquiring a first ultrasound image of an object, detecting a first nerve region corresponding to a first target nerve in the first ultrasound image, determining whether an abnormal region is present in the first nerve region of the first ultrasound image on the basis of a determination standard for determining whether a target nerve is abnormal, and displaying at least one of information about the abnormal region and basis information about a basis for determining the abnormal region on the basis of a result of determining whether the abnormal region is present in the first nerve region.

According to another embodiment, there is provided an ultrasound diagnostic apparatus including a probe configured to transmit an ultrasound signal to an object and receive an ultrasound signal reflected from the object, a user interface device, a display, a processor, and a memory configured to store instructions executable by the processor, wherein, the processor executes the instructions to acquire a first ultrasound image of the object on the basis of the reflected ultrasound signal, detect a first nerve region corresponding to a first target nerve in the first ultrasound image, determine whether an abnormal region is present in the first nerve region of the first ultrasound image on the basis of a determination standard for determining whether a target nerve is abnormal, and display at least one of information about the abnormal region and basis information about a basis for determining the abnormal region through the display on the basis of a result of determining whether the abnormal region is present in the first nerve region.

According to still another embodiment, there is provided a computer program stored in a medium to perform a method in combination with an ultrasound diagnostic apparatus, the method including acquiring a first ultrasound image of an object, detecting a first nerve region corresponding to a first target nerve in the first ultrasound image, determining whether an abnormal region is present in the first nerve region of the first ultrasound image on the basis of a determination standard for determining whether a target nerve is abnormal, and displaying at least one of information about the abnormal region and basis information about a basis for determining the abnormal region on the basis of a result of determining whether the abnormal region is present in the first nerve region.

Advantageous Effects

It is possible to determine whether an abnormality is present in a nerve region detected from an ultrasound image, and on the basis of the determination result, it is possible to provide information about an abnormal region of the nerve region or basis information about a basis for determining the abnormal region.

It is possible to detect a nerve region from an ultrasound image acquired in real time, and accurately provide information about whether a nerve is abnormal and basis information about a basis for determining the abnormality.

By providing basis information about a basis for determining that a nerve is abnormal, a user can accurately diagnose the nerve.

DESCRIPTION OF DRAWINGS

The present invention can be easily understood from the following detailed description and combination of the accompanying drawings, and reference numerals denote structural elements.

FIG. 1 is a block diagram illustrating a configuration of an ultrasound diagnostic apparatus according to one embodiment.

FIGS. 2A to 2C are views illustrating an ultrasound diagnostic apparatus according to one embodiment.

FIG. 9C is a view for describing honeycomb structures observed in normal nerves and honeycomb structures observed in abnormal nerves, according to one embodiment.

BEST MODE

Figure 2B:
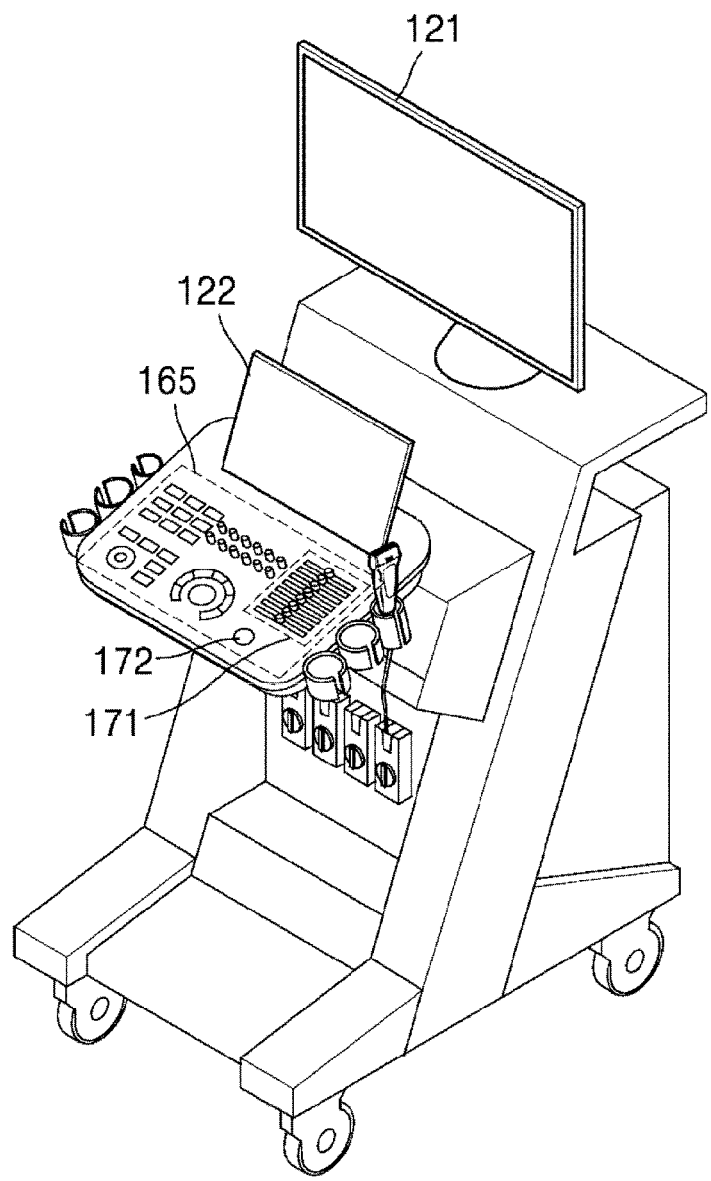

Disclosed is a method for operating an ultrasound diagnostic apparatus, the method including acquiring a first ultrasound image of an object, detecting a first nerve region corresponding to a first target nerve in the first ultrasound image, determining whether an abnormal region is present in the first nerve region of the first ultrasound image on the basis of a determination standard for determining whether a target nerve is abnormal, and displaying at least one of information about the abnormal region and basis information about a basis for determining the abnormal region on the basis of a result of determining whether the abnormal region is present in the first nerve region.

[Modes of the Invention]

The present specification describes the principles of the present invention and discloses embodiments such that the scope of the present invention may be clarified and those skilled in the art to which the present invention pertains may implement the present invention. The disclosed embodiments may be implemented in various forms.

Throughout the specification, like reference numerals refer to like elements. The present specification does not describe all components of embodiments, and common descriptions in the technical field to which the present invention pertains and redundant descriptions between the embodiments will be omitted. Terms such as "part" and "portion" used herein denote those that may be implemented by software or hardware, and according to embodiments, a plurality of parts or portions may be implemented by a single unit or element, or a single part or portion may include a plurality of units or elements. Hereinafter, an operation principle and the embodiments of the present invention will be described with reference to the accompanying drawings.

In the present specification, an image may include a medical image acquired by a medical imaging apparatus such as a magnetic resonance imaging (MRI) apparatus, a computed tomography (CT) apparatus, an ultrasound imaging apparatus, and an X-ray imaging apparatus.

In the present specification, the term "object" is a thing to be photographed and may include a person, an animal, or a part thereof. For example, the object may include a part of a body (i.e., an organ), a phantom, or the like.

Throughout the specification, the term "ultrasound image" refers to an image of an object, which is processed on the basis of an ultrasound signal transmitted to the object and reflected from the object.

Throughout the specification, the term "target nerve" refers to a nerve that is a target for determining whether there is an abnormality, and the term "target nerve region" refers to a region corresponding to the target nerve in an ultrasound image. For example, the target nerve is a nerve of the same type as a reference nerve and refers to a nerve to be examined or diagnosed.

Throughout the specification, the term "reference nerve" refers to a nerve that becomes a reference for determining whether an abnormality is present in a target nerve, and the term "reference nerve region" refers to a region corresponding to the reference nerve in an ultrasound image.

Hereinafter, embodiments will be described in detail with reference to the accompanying drawings.

FIG. 1 is a block diagram illustrating a configuration of an ultrasound diagnostic apparatus 100 according to one embodiment. The ultrasound diagnostic apparatus 100 according to one embodiment may include a probe 20, an ultrasound transceiver 110, a controller 120, an image processor 130, a display part 140, a storage part 150, a communication part 160, and an input part 170.

The ultrasound diagnostic apparatus 100 may be implemented not only in a cart type but also in a portable type. Examples of the portable ultrasound diagnostic apparatus may include a smart phone, a laptop computer, a personal digital assistant (PDA), a tablet personal computer (PC), or the like including a probe and an application, but the present invention is not limited thereto.

The probe 20 may include a plurality of transducers. The plurality of transducers may transmit an ultrasound signal to an object 10 according to a transmission signal applied from a transmitter 113. The plurality of transducers may receive the ultrasound signal reflected from the object 10 and form a received signal. In addition, the probe 20 may be implemented integrally with the ultrasound diagnostic apparatus 100 or may be implemented as a separate type connected to the ultrasound diagnostic apparatus 100 in a wired or wireless manner. In addition, the ultrasound diagnostic apparatus 100 may be provided with one or a plurality of probes 20 depending on an implementation form.

The controller 120 controls the transmitter 113 to form the transmission signal to be applied to each of the plurality of transducers in consideration of positions and focal points of the plurality of transducers included in the probe 20.

The controller 120 converts the received signal received from the probe 20 in an analog-to-digital conversion manner, and controls a receiver 115 to generate ultrasound data by summing the digitally converted received signals in consideration of the positions and focal points of the plurality of transducers.

The image processor 130 generates an ultrasound image using the ultrasound data generated by the receiver 115.

The display part 140 may display the generated ultrasound image and various pieces of information processed by the ultrasound diagnostic apparatus 100. The ultrasound diagnostic apparatus 100 may include one or a plurality of display parts 140 depending on the implementation form. In addition, the display part 140 may be implemented as a touch screen in combination with a touch panel.

The controller 120 may control the overall operation of the ultrasound diagnostic apparatus 100 and a signal flow between internal components of the ultrasound diagnostic apparatus 100. The controller 120 may include a memory that stores a program or data for performing a function of the ultrasound diagnostic apparatus 100, and a processor that processes the program or data. In addition, the controller 120 may control the operation of the ultrasound diagnostic apparatus 100 by receiving a control signal from the input part 170 or an external apparatus.

The ultrasound diagnostic apparatus 100 includes the communication part 160, and may be connected to the external apparatus (for example, a server, a medical apparatus, a portable apparatus (smart phone, tablet PC, wearable device, and the like)) through the communication part 160.

The communication part 160 may include one or more components enabling communication with the external apparatus, and may include, for example, at least one of a short-range communication module, a wired communication module, and a wireless communication module.

The communication part 160 may receive a control signal and data from the external apparatus and transmit the received control signal to the controller 120 so that the controller 120 may control the ultrasound diagnostic apparatus 100 in response to the received control signal.

Alternatively, the controller 120 may transmit a control signal to the external apparatus through the communication part 160 so that the external apparatus may be controlled in response to the control signal of the controller 120.

For example, the external apparatus may process data of an external apparatus in response to the control signal of the controller received through the communication part.

A program capable of controlling the ultrasound diagnostic apparatus 100 may be installed in the external apparatus, and the program may include instructions for performing some or all of the operations of the controller 120.

The program may be installed in the external apparatus in advance or may be installed by a user of the external apparatus by downloading the program from a server that provides applications. The server that provides applications may include a recording medium in which the corresponding program is stored.

The storage part 150 may store various types of data or programs for driving and controlling the ultrasound diagnostic apparatus 100, input/output ultrasound data, acquired ultrasound images, and the like.

The input part 170 may receive a user's input for controlling the ultrasound diagnostic apparatus 100. For example, the user's input may include an input for manipulating a button, a keypad, a mouse, a trackball, a jog switch, a knob, or the like, an input for touching a touchpad or a touch screen, a voice input, a motion input, and a biometric information input (e.g., iris recognition, fingerprint recognition, or the like), but the present invention is not limited thereto.

An example of the ultrasound diagnostic apparatus 100 according to one embodiment will be described below with reference to FIGS. 2A to 2C.

Figure 2C:
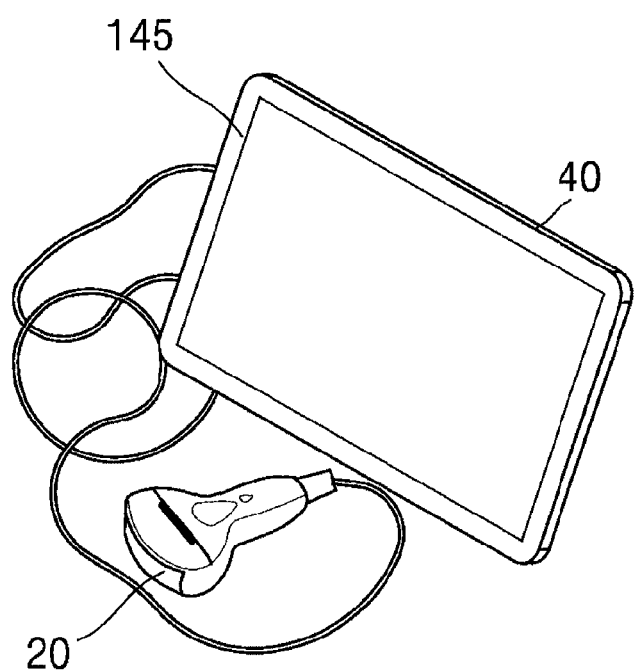

FIGS. 2A to 2C are views illustrating ultrasound diagnostic apparatuses according to one embodiment.

Referring to FIG. 2A and FIG. 2B, ultrasound diagnostic apparatuses 100a and 100b may each include a main display part 121 and a sub-display part 122. One or more of the main display part 121 and the sub-display part 122 may be implemented as a touch screen. The main display part 121 and the sub-display part 122 may display ultrasound images or various pieces of information processed by the ultrasound diagnostic apparatuses 100a and 100b. Further, the main display part 121 and the sub-display part 122 may each be implemented as a touch screen and receive data for controlling the ultrasound diagnostic apparatuses 100a and 100b from a user by providing a graphical user interface (GUI). For example, the main display part 121 may display the ultrasound image, and the sub-display part 122 may display a control panel for controlling the display of the ultrasound image in the form of a GUI. The sub-display part 122 may receive data for controlling the display of the image through the control panel displayed in the form of a GUI. The ultrasound diagnostic apparatuses 100a and 100b may control the display of the ultrasound image displayed on the main display part 121 using input control data.

Referring to FIG. 2B, the ultrasound diagnostic apparatus 100b may further include a control panel 165 in addition to the main display part 121 and the sub-display part 122. The control panel 165 may include a button, a trackball, a jog switch, a knob, or the like, and may receive data for controlling the ultrasound diagnostic apparatus 100b from the user. For example, the control panel 165 may include a time gain compensation (TGC) button 171, a freeze button 172, and the like. The TGC button 171 is a button for setting a TGC value for each depth of the ultrasound image. In addition, when an input of the freeze button 172 is detected while scanning the ultrasound image, the ultrasound diagnostic apparatus 100b may maintain a state in which a frame image of the corresponding time point is displayed.

Meanwhile, the button, the trackball, the jog switch, the knob, or the like included in the control panel 165 may be provided to the GUI on the main display part 121 or the sub-display part 122.

Referring to FIG. 2C, an ultrasound diagnostic apparatus 100c may be implemented in a portable type. Examples of the portable ultrasound diagnostic apparatus 100c may include a smart phone, a laptop computer, a PDA, a tablet PC, or the like including a probe and an application, but the present invention is not limited thereto.

The ultrasound diagnostic apparatus 100c may include a probe 20 and a main body 40, and the probe 20 may be connected to one side of the main body 40 in a wired or wireless manner. The main body 40 may include a touch screen 145. The touch screen 145 may display ultrasound images, various pieces of information processed by the ultrasound diagnostic apparatus, a GUI, and the like.

Figure 3:
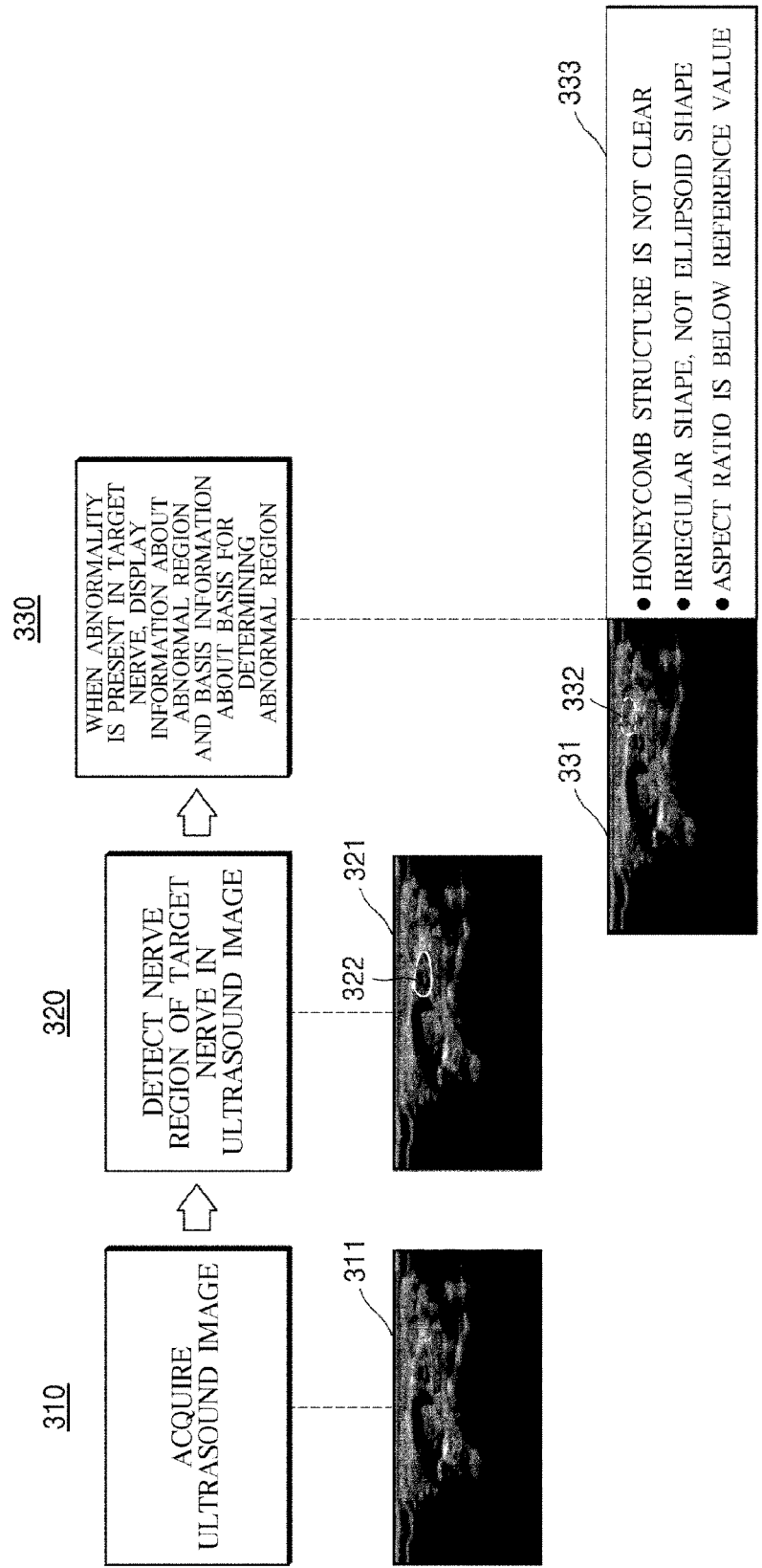
FIG. 3 is a view for schematically describing a process of detecting a nerve region of a target nerve in an ultrasound image to determine whether there is an abnormality, and displaying the determination result, according to one embodiment.

FIG. 3 is a view for schematically describing a process of detecting a nerve region of a target nerve in an ultrasound image to determine whether there is an abnormality, and displaying the determination result, according to one embodiment.

Referring to block 310 of FIG. 3, the ultrasound diagnostic apparatus 100 may acquire an ultrasound image of an object. For example, the ultrasound image may be an image obtained by scanning a target nerve, and may include a nerve region corresponding to the target nerve. As shown in an image 311, the ultrasound diagnostic apparatus 100 may display the ultrasound image on a display of the ultrasound diagnostic apparatus 100.

Referring to block 320 of FIG. 3, the ultrasound diagnostic apparatus 100 may detect a nerve region corresponding to the target nerve in the ultrasound image on the basis of an algorithm for detecting the nerve region. As shown in an image 321, the ultrasound diagnostic apparatus 100 may display a nerve region 322 in the ultrasound image.

Referring to block 330 of FIG. 3, the ultrasound diagnostic apparatus 100 may determine whether an abnormality is present in the target nerve of the ultrasound image on the basis of a determination standard for determining whether a target nerve is abnormal. When an abnormality is present in the target nerve, the ultrasound diagnostic apparatus 100 may detect an abnormal region in the nerve region. As shown in an image 331, the ultrasound diagnostic apparatus 100 may display an abnormal region 332 on the ultrasound image. In addition, the ultrasound diagnostic apparatus 100 may display information about the abnormal region and basis information 333 about the basis for determining the abnormal region.

Figure 4:
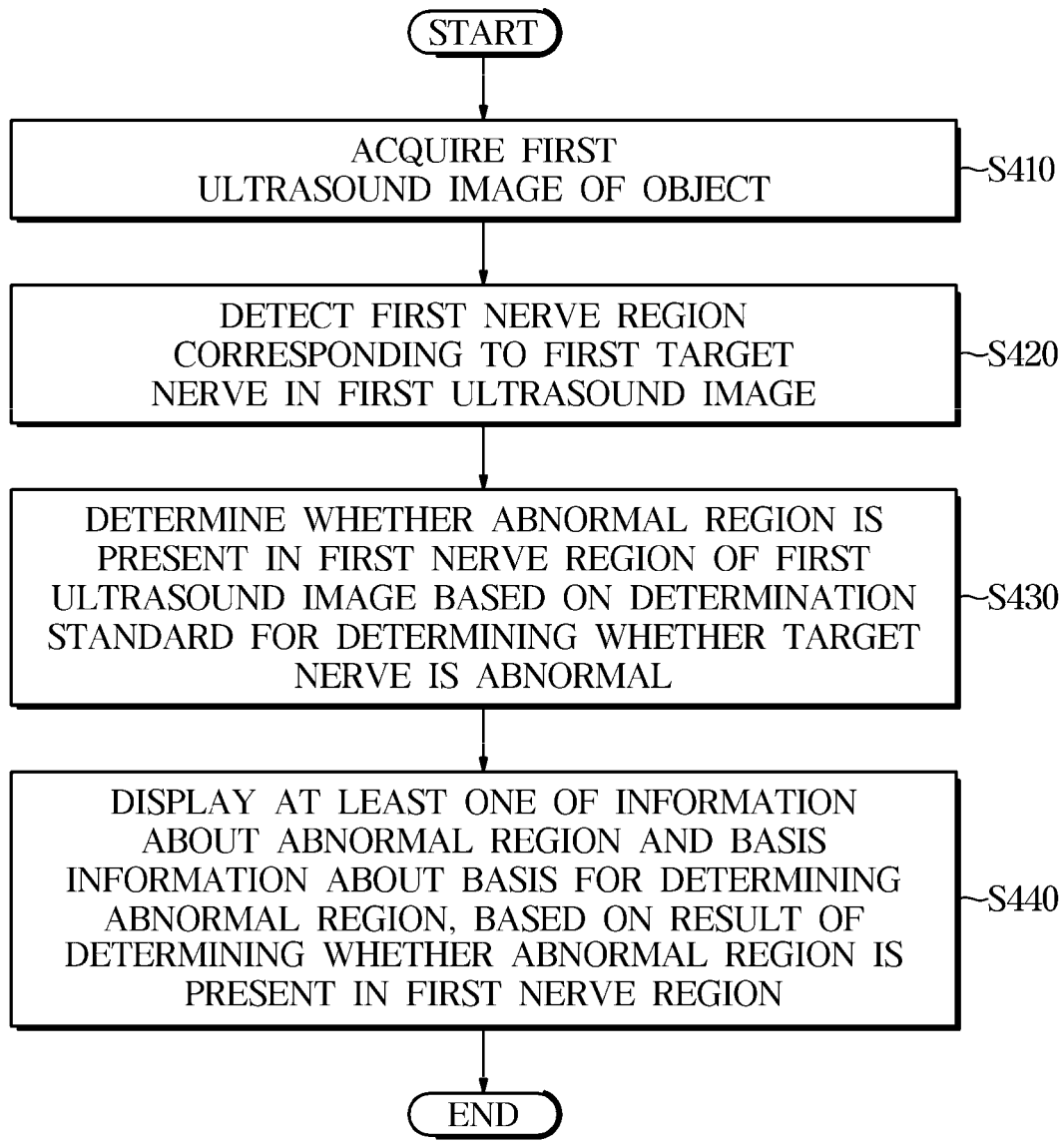
FIG. 4 is a view for describing a method for operating the ultrasound diagnostic apparatus according to one embodiment.

FIG. 4 is a view for describing a method for operating the ultrasound diagnostic apparatus according to one embodiment.

Referring to FIG. 4, in operation S410, the ultrasound diagnostic apparatus 100 may acquire a first ultrasound image of an object. For example, the probe in the ultrasound diagnostic apparatus 100 may transmit an ultrasound signal to a region including a first target nerve of the object, and may receive the ultrasound signal reflected from the region including the first target nerve. The ultrasound diagnostic apparatus 100 may acquire the first ultrasound image for the first target nerve on the basis of the reflected ultrasound signal. The first ultrasound image may be acquired in real time. For example, the first ultrasound image may be acquired in units of an image or video.

In operation S420, the ultrasound diagnostic apparatus 100 may detect a first nerve region corresponding to the first target nerve in the first ultrasound image.

For example, the ultrasound diagnostic apparatus 100 may detect the first nerve region corresponding to the first target nerve in the first ultrasound image on the basis of a predetermined automatic detection algorithm or a predetermined automatic segmentation algorithm. The ultrasound diagnostic apparatus 100 may display the detected first nerve region on the first ultrasound image. In addition, the ultrasound diagnostic apparatus 100 may display only the detected first nerve region. A process of detecting the nerve region from the ultrasound image will be described with reference to FIG. 5.

In operation S430, the ultrasound diagnostic apparatus 100 may determine whether an abnormal region is present in the first nerve region of the first ultrasound image on the basis of the determination standard for determining whether a target nerve is abnormal.

For example, the determination standard may be acquired on the basis of at least one of an anatomical structure in a reference nerve region for a reference nerve, a shape of the reference nerve region, and a size of the reference nerve region. Here, the anatomical structure may be determined on the basis of the shape, size, and relative positional relationship of structures constituting the nerve.

For example, the ultrasound diagnostic apparatus 100 may determine whether an abnormality is present in the first target nerve on the basis of a honeycomb structure that is an anatomical structure observed in a first target nerve region.

Specifically, the ultrasound diagnostic apparatus 100 may determine whether an abnormal region is present in the first nerve region corresponding to the first target nerve on the basis of a similarity between a reference honeycomb structure in the reference nerve region for the reference nerve and a target honeycomb structure in a target nerve region for the target nerve. A process of determining whether the nerve is abnormal on the basis of the honeycomb structure observed in the ultrasound image will be described with reference to FIG. 6.

For example, the ultrasound diagnostic apparatus 100 may acquire a learning model for determining whether the target nerve is abnormal using the similarity between the reference honeycomb structure and the target honeycomb structure. The ultrasound diagnostic apparatus 100 may apply the first nerve region to the learning model to detect a region in which an abnormal honeycomb structure exists in the first nerve region.

Here, the learning model may be a model in which the reference honeycomb structure is learned on the basis of at least one of a shape and pattern of a honeycomb structure included in a plurality of ultrasound images and a structure of a peripheral region of the honeycomb structure. In addition, the learning model may be a model for determining whether a predetermined target nerve is abnormal when an ultrasound image in which a target honeycomb structure is included in the predetermined target nerve is acquired.

For example, the ultrasound diagnostic apparatus 100 may acquire the similarity on the basis of a matching rate between the reference honeycomb structure in the reference nerve region of a reference template for the reference nerve and a first target honeycomb structure in the first nerve region. The ultrasound diagnostic apparatus 100 may determine whether an abnormal region is present in the first nerve region corresponding to the first target nerve on the basis of the acquired similarity. The learning model for acquiring the similarity between the reference honeycomb structure and the target honeycomb structure and determining whether the target nerve is abnormal using the similarity will be described with reference to FIGS. 9A and 9B.

For example, the ultrasound diagnostic apparatus 100 may acquire the similarity on the basis of at least one of corner information and feature point information for each of the reference honeycomb structure in the reference nerve region for the reference nerve and the first target honeycomb structure in the first nerve region. The ultrasound diagnostic apparatus 100 may determine whether an abnormal region is present in the first nerve region corresponding to the first target nerve on the basis of the acquired similarity.

For example, the ultrasound diagnostic apparatus 100 may determine whether an abnormal region is present in the first nerve region corresponding to the first target nerve on the basis of a second determination standard for determining whether a target nerve is abnormal using a difference between a reference aspect ratio of the reference nerve region for the reference nerve and an aspect ratio of the target nerve region for the target nerve. A process of determining whether the target nerve is abnormal on the basis of the aspect ratio of the target nerve region will be described with reference to FIG. 7.

For example, the ultrasound diagnostic apparatus 100 may determine whether an abnormal region is present in the first nerve region corresponding to the first target nerve on the basis of a third determination standard for determining whether a target nerve is abnormal using a difference between a size of a reference cross-sectional area of the reference nerve region for the reference nerve and a size of a cross-sectional area of the target nerve region for the target nerve. A process of determining whether the target nerve is abnormal on the basis of the size of the cross-sectional area of the target nerve region will be described with reference to FIG. 8.

For example, the ultrasound diagnostic apparatus 100 may acquire a reference value of at least one parameter, which becomes a reference for determining whether the target nerve is abnormal. For example, the parameter may include at least one of Validity of the honeycomb structure observed in the nerve region, the similarity of the honeycomb structure, the shape of the nerve region, the aspect ratio of the nerve region, and the size of the cross-sectional area of the nerve region, and the present invention is not limited to the above examples. The ultrasound diagnostic apparatus 100 may determine that an abnormal region is present in the first nerve region when a difference between a value of at least one parameter acquired from the first ultrasound image and the reference value of at least one parameter is out of a preset range.

In operation S440, the ultrasound diagnostic apparatus 100 may display at least one of information about the abnormal region and basis information about the basis for determining the abnormal region, on the basis of the result of determining whether an abnormal region is present in the first nerve region.

For example, the basis information about the basis for determining the abnormal region may include information about at least one parameter, which becomes a reference for determining whether the first target nerve is abnormal, and information obtained by comparing the value of at least one parameter and the reference value of at least one parameter.

For example, the ultrasound diagnostic apparatus 100 may display a boundary of the abnormal region on the first ultrasound image. The ultrasound diagnostic apparatus 100 may display the bases for determining whether an abnormal region is present in the first nerve region according to a preset priority. For example, the preset priority may be determined on the basis of a degree to which values of the parameters, which become a reference for determining whether the first target nerve is abnormal, are out of the preset range.

For example, the ultrasound diagnostic apparatus 100 may display the information about the abnormal region on the first ultrasound image. The ultrasound diagnostic apparatus 100 may display trend information of the abnormal region for the object by referring to a previous ultrasound image for the object.

Figure 5:
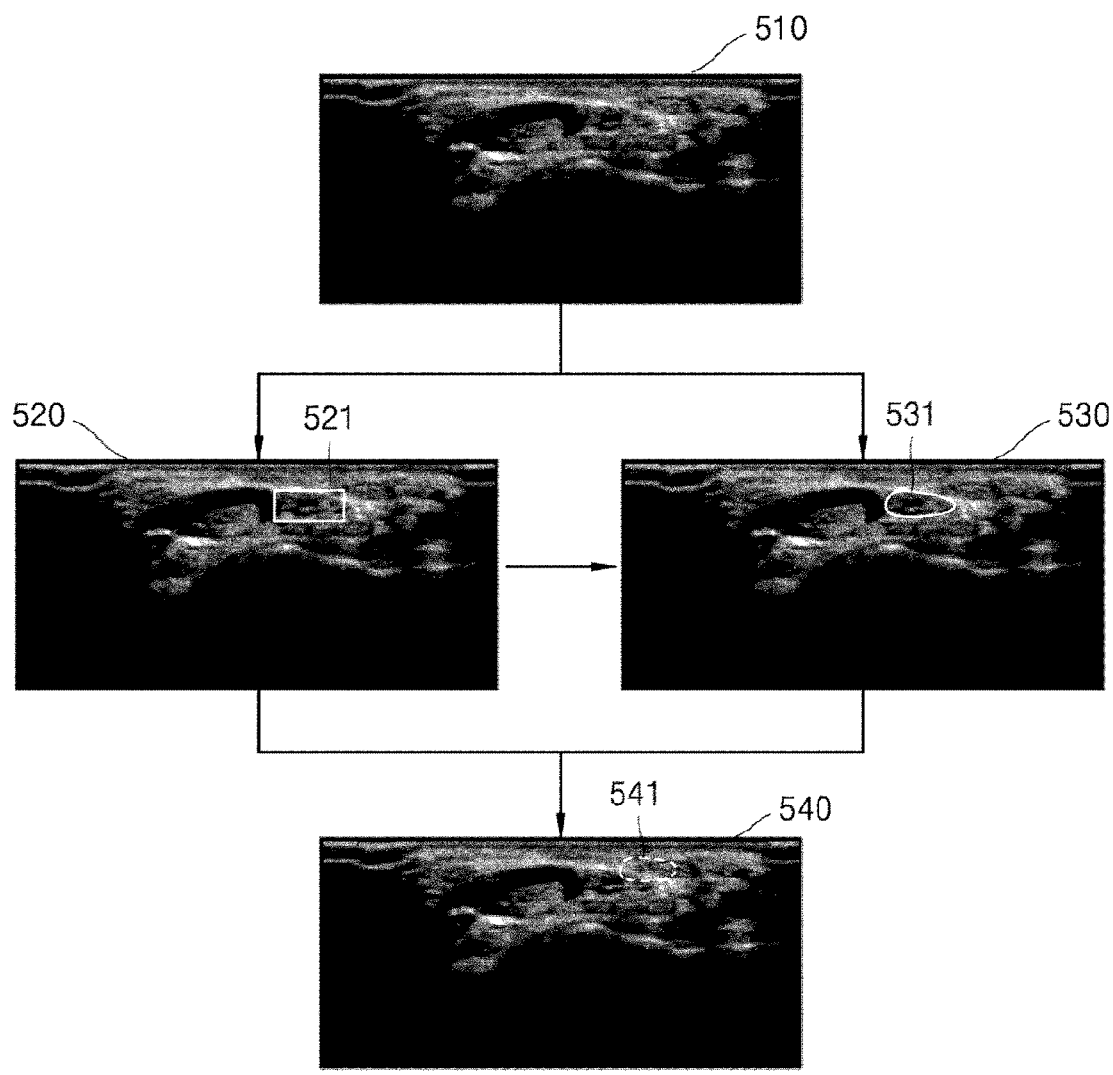
FIG. 5 is a view for describing a process of detecting a nerve region from an ultrasound image and displaying an abnormal region in the ultrasound image, according to one embodiment.

FIG. 5 is a view for describing a process of detecting a nerve region from an ultrasound image and displaying an abnormal region in the ultrasound image, according to one embodiment.

The ultrasound diagnostic apparatus 100 may acquire a first ultrasound image for a first target nerve. An image 510 of FIG. 5 represents the first ultrasound image for the first target nerve.

For example, the ultrasound diagnostic apparatus 100 may acquire the first ultrasound image in real time using the probe in the ultrasound diagnostic apparatus 100, or acquire the first ultrasound image from ultrasound images stored in the ultrasound diagnostic apparatus 100. In addition, the ultrasound diagnostic apparatus 100 may receive the first ultrasound image from the external apparatus.

The ultrasound diagnostic apparatus 100 may detect a first nerve region corresponding to the first target nerve in the first ultrasound image. For example, the ultrasound diagnostic apparatus 100 may analyze the entire region of the first ultrasound image and detect the first nerve region corresponding to the first target nerve using a predetermined automatic detection algorithm. For example, the predetermined automatic detection algorithm may be a learning model that detects a nerve region corresponding to a target nerve in an ultrasound image. An image 520 of FIG. 5 represents an image in which a region 521 detected as the first nerve region is displayed on the first ultrasound image. In addition, when a cross section observed in the first ultrasound image, which is acquired in real time, is changed according to the movement of the probe, the first nerve region may be automatically tracked according to the changed cross-section, and the first nerve region may be displayed. That is, the ultrasound diagnostic apparatus 100 may track and display only the detected first nerve region. For example, the ultrasound diagnostic apparatus 100 may display the first nerve region with a bounding box as shown in the image 520 of FIG. 5. Here, a strength of a boundary represented by the bounding box may be adjusted.

Further, the ultrasound diagnostic apparatus 100 may detect the first nerve region corresponding to the first target nerve by segmenting the first ultrasound image into a plurality of regions using a predetermined automatic segmentation algorithm and analyzing the entire segmented plurality of regions. For example, the predetermined automatic segmentation algorithm may be a learning model for detecting a nerve region corresponding to a target nerve by segmenting an ultrasound image into a plurality of regions and analyzing the segmented regions. An image 530 of FIG. 5 represents an image in which a region 531 detected as the first nerve region is displayed on the first ultrasound image. In addition, the ultrasound diagnostic apparatus 100 may precisely detect the region 531 in the first nerve region by analyzing the region 521 detected as the first nerve region from the image 520 of FIG. 5 on the basis of the predetermined automatic segmentation algorithm.

Meanwhile, in the ultrasound diagnostic apparatus 100, the first nerve region corresponding to the first target nerve may also be determined in the first ultrasound image on the basis of a user's input.

The ultrasound diagnostic apparatus 100 may determine whether an abnormal region is present in the first nerve region of the first ultrasound image on the basis of a determination standard for determining whether a target nerve is abnormal. When it is determined that the abnormal region is present in the first nerve region, the ultrasound diagnostic apparatus 100 may detect the abnormal region in the first nerve region and display the abnormal region. An image 540 of FIG. 5 represents an image in which an abnormal region 541 in the first nerve region is displayed on the first ultrasound image.

Figure 6:
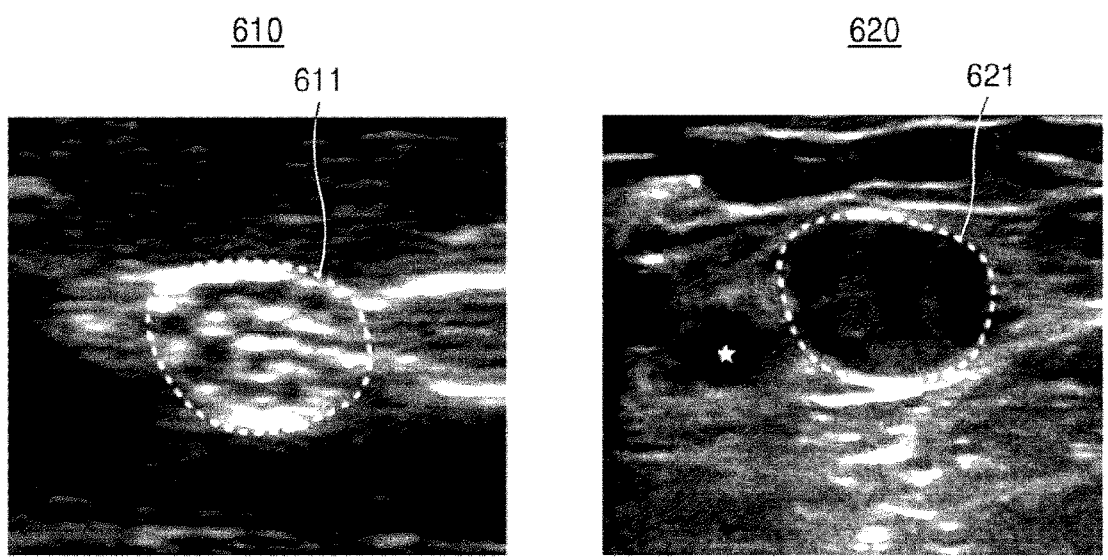
FIG. 6 is a view for describing a process of determining whether a nerve is abnormal on the basis of an anatomical structure in a nerve region in an ultrasound image, according to one embodiment.

FIG. 6 is a view for describing a process of determining whether a nerve is abnormal on the basis of an anatomical structure in a nerve region in an ultrasound image, according to one embodiment.

The ultrasound diagnostic apparatus 100 may determine whether an abnormal region is present in the first nerve region of the first ultrasound image on the basis of a determination standard for determining whether a target nerve is abnormal, which is acquired on the basis of the anatomical structure in a reference nerve region for a reference nerve.

For example, the ultrasound diagnostic apparatus 100 may determine whether an abnormal region is present in the first nerve region of the first ultrasound image on the basis of a first determination standard for determining whether a target nerve is abnormal using a honeycomb structure representing a structure observed in a nerve region.

For example, the first determination standard may be a reference for determining whether a target nerve is abnormal using a similarity between a reference honeycomb structure in the reference nerve region and a target honeycomb structure in the target nerve region. Here, the reference honeycomb structure represents a structure observed in the reference nerve region. Further, the reference honeycomb structure may also be a structure that is observed in a nerve region of a normal nerve. For example, the similarity may indicate a matching rate between the reference honeycomb structure and the target honeycomb structure.

For example, the similarity between the reference honeycomb structure and the target honeycomb structure may be acquired on the basis of at least one of a learning model, template matching, information about a feature point, and corner information.

For example, the ultrasound diagnostic apparatus 100 may acquire the learning model for determining whether a target nerve is abnormal using the similarity between the reference honeycomb structure and the target honeycomb structure. The ultrasound diagnostic apparatus 100 may acquire the similarity between the reference honeycomb structure and the first target honeycomb structure in the first nerve region by applying the first nerve region to the learning model. The learning model for acquiring the similarity between the reference honeycomb structure and the target honeycomb structure and determining whether the target nerve is abnormal using the similarity will be described with reference to FIGS. 9A and 9B.

For another example, the ultrasound diagnostic apparatus 100 may acquire the similarity on the basis of a matching rate between the reference honeycomb structure in the reference nerve region of a reference template for the reference nerve and the first target honeycomb structure in the first nerve region. For a specific example, the ultrasound diagnostic apparatus 100 may store a plurality of reference templates for the reference nerve. The ultrasound diagnostic apparatus 100 may detect the first target honeycomb structure in the first nerve region of the first ultrasound image. The ultrasound diagnostic apparatus 100 may acquire a first reference honeycomb structure having a structure most similar to the first target honeycomb structure by comparing the reference honeycomb structure of each of the plurality of reference templates with the first target honeycomb structure. The ultrasound diagnostic apparatus 100 may acquire the similarity indicating the matching rate between the first reference honeycomb structure and the first target honeycomb structure on the basis of the shape or pattern of the first target honeycomb structure and the first reference honeycomb structure.

For still another example, the ultrasound diagnostic apparatus 100 may acquire the similarity on the basis of at least one of corner information and feature point information for each of the reference honeycomb structure in the reference nerve region and the first target honeycomb structure in the first nerve region. For a specific example, the ultrasound diagnostic apparatus 100 may detect reference feature points, which may specify the honeycomb structure, on the basis of the reference honeycomb structure. The ultrasound diagnostic apparatus 100 may detect feature points corresponding to the reference feature points from the first target honeycomb structure in the first nerve region. The ultrasound diagnostic apparatus 100 may acquire information about the reference feature points, which includes at least one piece of information about the number, a location, a distribution degree, a maximum brightness value, a minimum brightness value, and an average value of brightness values of the reference feature points. In addition, the ultrasound diagnostic apparatus 100 may acquire information about the feature points, which includes at least one piece of information about the number, a location, a distribution degree, a maximum brightness value, a minimum brightness value, and an average value of brightness values of the feature points corresponding to the reference feature points. The ultrasound diagnostic apparatus 100 may compare values of at least one parameter on the basis of the information about the reference feature points and the information about the feature points, and acquire the similarity on the basis of the comparison result. A process of acquiring the similarity using the corner information and determining whether a target nerve is abnormal according to the similarity will be described with reference to FIG. 10.

Meanwhile, when the similarity is greater than or equal to a preset similarity, the ultrasound diagnostic apparatus 100 may determine that the first target nerve is normal. An image 610 of FIG. 6 is a view illustrating a normal first target honeycomb structure 611 observed in the first nerve region corresponding to the first target nerve. On the other hand, when the similarity is less than the preset similarity, the ultrasound diagnostic apparatus 100 may determine that an abnormality is present in the first target nerve. For example, the ultrasound diagnostic apparatus 100 may detect a region, in which an abnormal honeycomb structure exists, in the first nerve region corresponding to the first target nerve on the basis of the learning model. An image 620 of FIG. 6 is a view illustrating an abnormal first target honeycomb structure 621 observed in the first nerve region corresponding to the first target nerve. Honeycomb structures observed in normal nerves and honeycomb structures observed in abnormal nerves will be described with reference to FIG. 9C.

Figure 7:
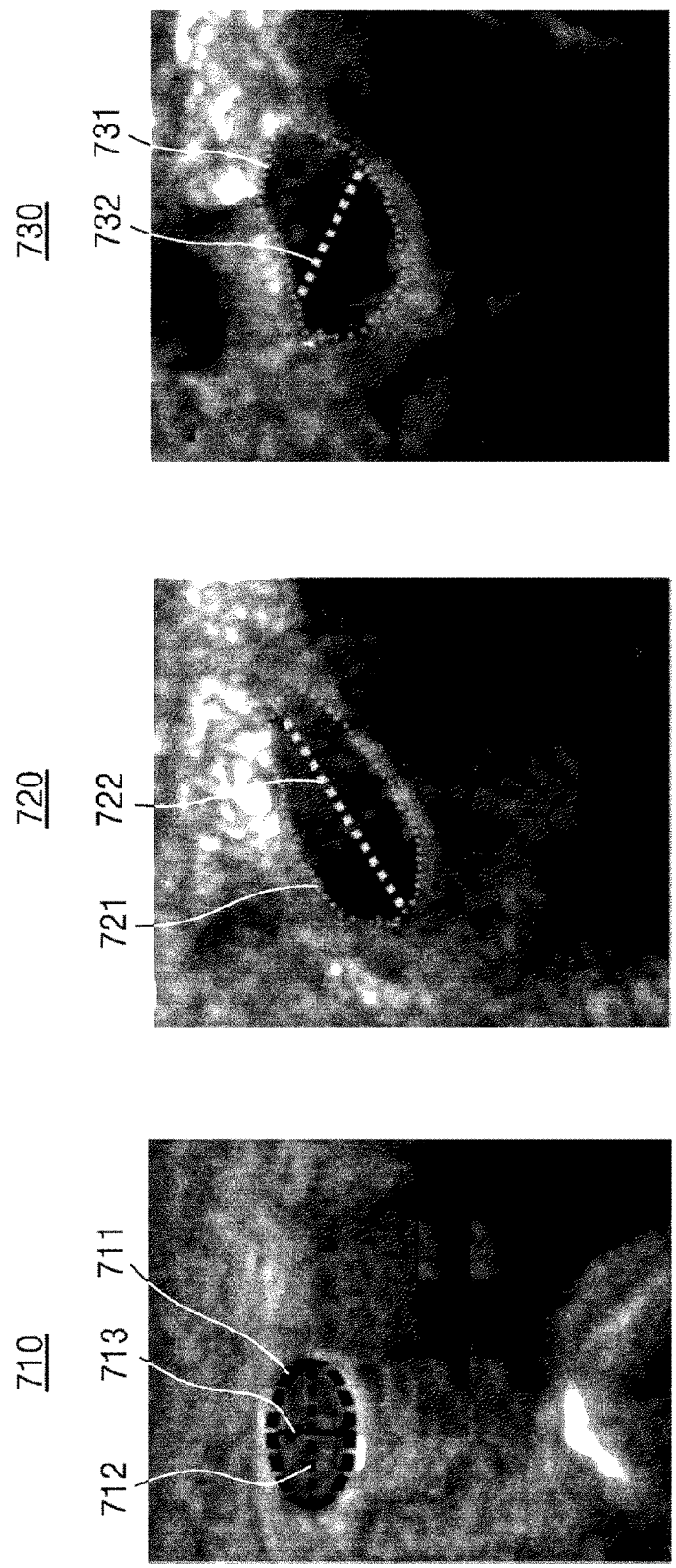
FIG. 7 is a view for describing a process of determining whether a nerve is abnormal on the basis of a shape of a nerve region in an ultrasound image, according to one embodiment.

FIG. 7 is a view for describing a process of determining whether a nerve is abnormal on the basis of a shape of a nerve region in an ultrasound image, according to one embodiment.

The ultrasound diagnostic apparatus 100 may determine whether an abnormal region is present in a first nerve region corresponding to the first target nerve on the basis of a second determination standard for determining whether a target nerve is abnormal using a difference between a reference aspect ratio of a reference nerve region for a reference nerve and an aspect ratio of a target nerve region for the target nerve.

Referring to an image 710 of FIG. 7, the aspect ratio may indicate a ratio of a length of a major axis 712 to a length of a minor axis 713 in a nerve region 711. In addition, the aspect ratio may also indicate a ratio of the length of the minor axis 713 to the length of the major axis 712 in the nerve region 711.

An image 720 of FIG. 7 is a view for describing a method of detecting a major axis in a nerve region 721. For example, the ultrasound diagnostic apparatus 100 may detect a center of gravity in the nerve region 721. The ultrasound diagnostic apparatus 100 may detect a line segment 722, which is the longest among line segments each having intersecting points between a straight line passing through the center of gravity of the nerve region 721 and the nerve region 721 as both end points, as the major axis.

An image 730 of FIG. 7 is a view for describing a method of detecting a minor axis in a nerve region 731. For example, the ultrasound diagnostic apparatus 100 may detect a center of gravity in the nerve region 731. The ultrasound diagnostic apparatus 100 may detect a line segment 732, which is the shortest among line segments each having intersecting points between a straight line passing through the center of gravity of the nerve region 731 and the nerve region 731 as both end points, as the minor axis.

The ultrasound diagnostic apparatus 100 may acquire the reference aspect ratio of the reference nerve region for the reference nerve. For example, the reference aspect ratio may be set by the user or acquired from the external apparatus. The ultrasound diagnostic apparatus 100 may acquire the first ultrasound image for the first target nerve and detect the first nerve region corresponding to the first target nerve from the first ultrasound image. The ultrasound diagnostic apparatus 100 may acquire a length of a major axis and a length of a minor axis for the first nerve region. The ultrasound diagnostic apparatus 100 may calculate an aspect ratio representing a ratio of the length of the major axis to the length of the minor axis. When a difference between the reference aspect ratio and the aspect ratio is within a preset range, the ultrasound diagnostic apparatus 100 may determine that the first target nerve is normal. On the other hand, when the difference between the reference aspect ratio and the aspect ratio is outside the preset range, the ultrasound diagnostic apparatus 100 may determine that an abnormality is present in the first target nerve. That is, the ultrasound diagnostic apparatus 100 may determine the first nerve region, whose aspect ratio is calculated, as the abnormal region. When there are a plurality of nerve regions corresponding to the first target nerve in the first ultrasound image, the ultrasound diagnostic apparatus 100 may calculate an aspect ratio for each of the plurality of nerve regions, and detect an abnormal nerve region on the basis of the result of comparison between the calculated aspect ratio and the reference aspect ratio.

Figure 8:
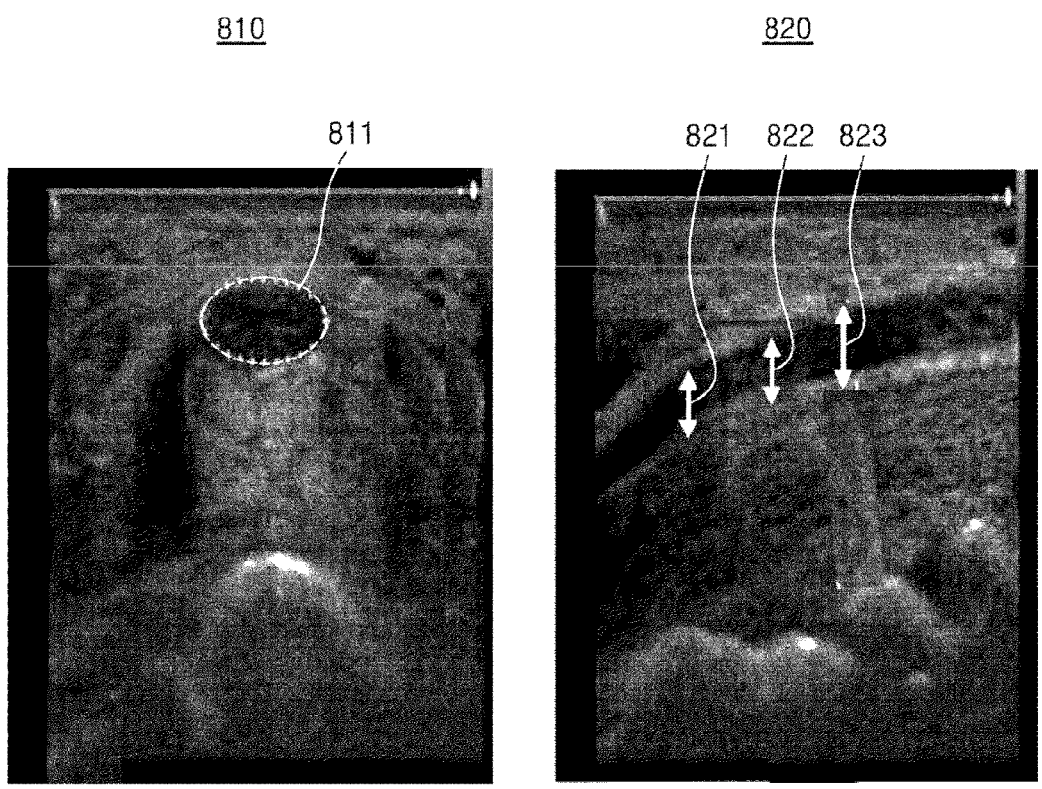
FIG. 8 is a view for describing a process of determining whether a nerve is abnormal on the basis of a size of a cross-sectional area of a nerve region in an ultrasound image, according to one embodiment.

FIG. 8 is a view for describing a process of determining whether a nerve is abnormal on the basis of a size of a cross-sectional area of a nerve region in an ultrasound image, according to one embodiment.

The ultrasound diagnostic apparatus 100 may determine whether an abnormal region is present in a first nerve region corresponding to the first target nerve on the basis of a third determination standard for determining whether a target nerve is abnormal using a difference between a size of a cross-sectional area of a reference nerve region for a reference nerve and a size of a cross-sectional area of a target nerve region for the target nerve.

When a nerve is compressed, a size of a cross-sectional area of the nerve may be less than a size of a reference cross-sectional area. Here, the size of the reference cross-sectional area may be a threshold value that becomes a reference to determine that a nerve is normal. For example, the size of the reference cross-sectional area for the reference nerve may be set by the user or acquired from the external apparatus.

Referring to an image 810 of FIG. 8, the ultrasound diagnostic apparatus 100 may acquire a first ultrasound image for the first target nerve and detect a first nerve region 811 corresponding to the first target nerve from the first ultrasound image. The ultrasound diagnostic apparatus 100 may calculate a size of a cross-sectional area of the first nerve region 811. When the size of the cross-sectional area of the first nerve region 811 is equal to or greater than the size of the reference cross-sectional area, the ultrasound diagnostic apparatus 100 may determine that the first target nerve 811 is normal. On the other hand, when the size of the cross-sectional area of the first nerve region 811 is less than the size of the reference cross-sectional area, the ultrasound diagnostic apparatus 100 may determine that an abnormality is present in the first target nerve. That is, the ultrasound diagnostic apparatus 100 may determine the first nerve region 811, in which the size of the cross-sectional area is calculated, as the abnormal region.

Meanwhile, when there are a plurality of nerve regions corresponding to the first target nerve in the first ultrasound image, the ultrasound diagnostic apparatus 100 may calculate a size of a cross-sectional area for each of the plurality of nerve regions, and detect an abnormal nerve region on the basis of the result of comparison between the calculated size of the cross-sectional area and the size of the reference cross-sectional area.

Referring to an image 820 of FIG. 8, the ultrasound diagnostic apparatus 100 may detect a first nerve region corresponding to the first target nerve in a first ultrasound image. For example, a cross-sectional area of the first nerve region may be an area of a cross-section in a direction perpendicular to a length direction. Referring to the image 820 of FIG. 8, the size of the cross-sectional area of the first nerve region decreases from the length direction on the right side to the length direction on the left side. Lengths of diameters of the cross-section may increase in the order of a first diameter 821, a second diameter 822, and a third diameter 823. The ultrasound diagnostic apparatus 100 may calculate a first cross-sectional area corresponding to the first diameter 821, a second cross-sectional area corresponding to the second diameter 822, and a third cross-sectional area corresponding to the third diameter 823. Among the first to third cross-sectional areas, the first cross-sectional area may have a size less than the size of the reference cross-sectional area. The ultrasound diagnostic apparatus 100 may determine that an abnormality is present in the first target nerve. The ultrasound diagnostic apparatus 100 may determine a region, whose size is equal to the size of the first cross-sectional area, in the first nerve region as the abnormal region.

Figure 9A:
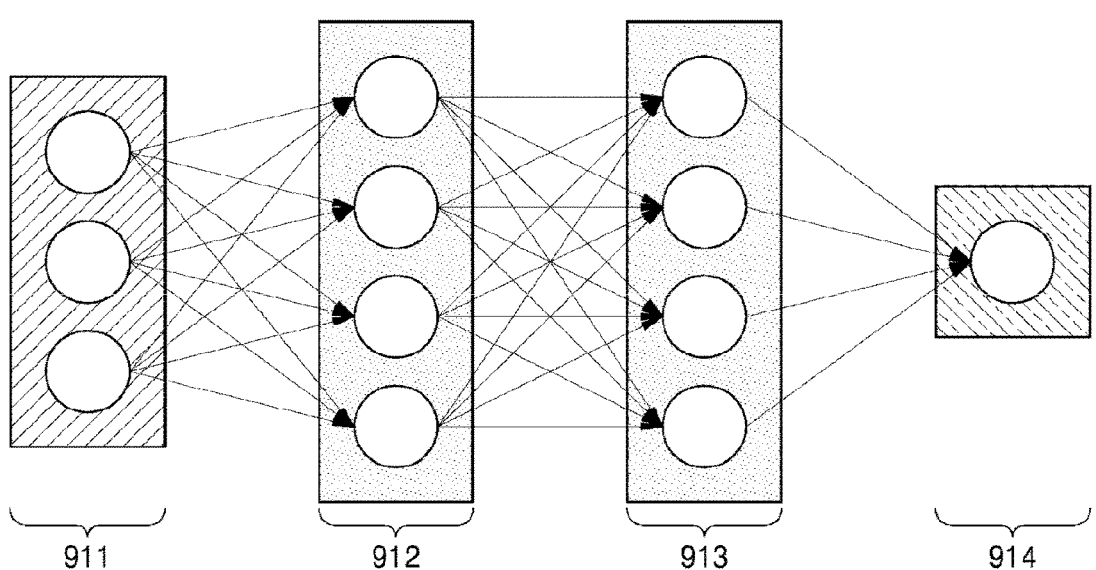
FIG. 9A is a view schematically illustrating an artificial neural network used to determine whether a nerve in an ultrasound image is abnormal, according to one embodiment.

FIG. 9A is a view schematically illustrating an artificial neural network used to determine whether a nerve in an ultrasound image is abnormal, according to one embodiment.

The learning model for acquiring a similarity between a reference honeycomb structure and a target honeycomb structure and determining whether a target nerve is abnormal using the similarity may be generated on the basis of a structure of the artificial neural network.

Referring to FIG. 9A, the artificial neural network may include an input layer 911, one or more hidden layers 912 and 913, and an output layer 914. Operations through the artificial neural network may be performed in a processor in a server or a processor in the ultrasound diagnostic apparatus 100. Here, the server may be a server that manages software, programs, data, files, and the like used in the ultrasound diagnostic apparatus 100. The processor in the server may store and manage programs including the learning model for determining whether a target nerve is abnormal in the server. The server may transmit the programs including the learning model to the ultrasound diagnostic apparatus 100.

Meanwhile, a weight between each layer and a node may be trained through learning and training performed in the hidden layers 912 and 913. For example, the processor of the server or the processor of the ultrasound diagnostic apparatus 100 may acquire a value of the weight between the nodes and the hidden layers 912 and 913 configured to determine a shape or pattern of a honeycomb structure observed in a nerve region or a structure of a peripheral region of the honeycomb structure through repetitive learning. The processor of the server or the processor of the ultrasound diagnostic apparatus 100 may determine whether a nerve is abnormal on the basis of a nerve region included in an ultrasound image and generate a learning model that detects an abnormal region using the artificial neural network trained by applying the acquired weight value.

Figure 9B:
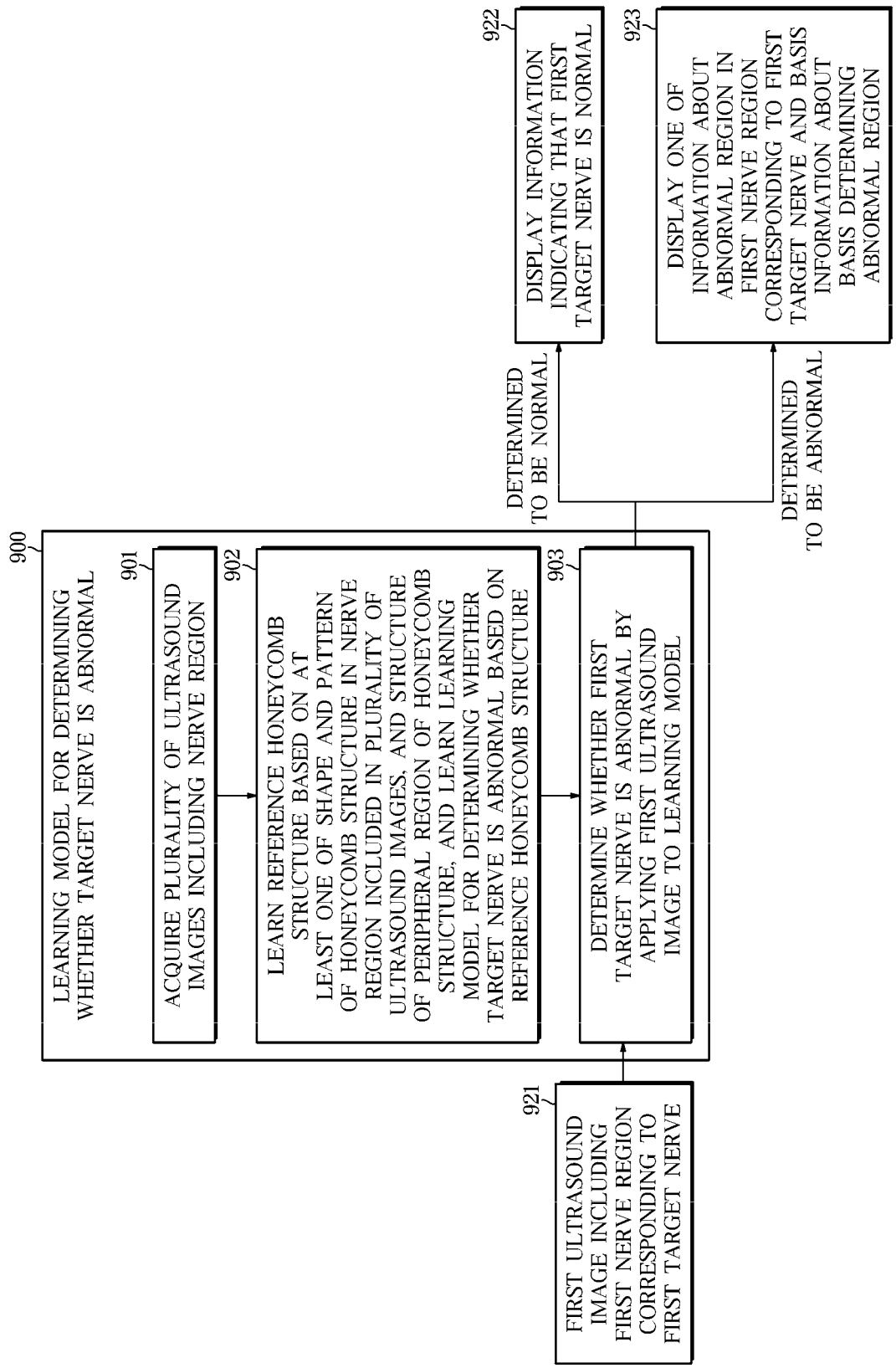
FIG. 9B is a view for describing a method of generating a learning model for determining whether a nerve in an ultrasound image is abnormal and an operation of the learning model, according to one embodiment.

FIG. 9B is a view for describing a method of generating a learning model for determining whether a nerve in an ultrasound image is abnormal and an operation of the learning model, according to one embodiment.

The server or the ultrasound diagnostic apparatus 100 may use a learning model 900 for determining whether a target nerve is abnormal to determine whether the first target nerve observed in the first ultrasound image is abnormal and detect the abnormal region.

At operation 901 of the learning model 900, the server or the ultrasound diagnostic apparatus 100 may acquire a plurality of ultrasound images including a nerve region. Here, the plurality of ultrasound images may include ultrasound images for a normal nerve and ultrasound images for an abnormal nerve.

For example, the server or the ultrasound diagnostic apparatus 100 may acquire the plurality of ultrasound images and information about whether the nerve included in the plurality of ultrasound images is abnormal as input data.

Further, the server or the ultrasound diagnostic apparatus 100 may acquire at least one of data on a shape and pattern of a honeycomb structure observed in the normal nerve and a structure of a peripheral region of the honeycomb structure and at least one of data on a shape and pattern of a honeycomb structure observed in the abnormal nerve and a structure of a peripheral region of the honeycomb structure as input data.

In operation 902 of the learning model 900, the server or the ultrasound diagnostic apparatus 100 may learn a reference honeycomb structure on the basis of at least one of a shape and pattern of a honeycomb structure in the nerve region included in the plurality of ultrasound images, and a structure of a peripheral region of the honeycomb structure. In addition, the server or the ultrasound diagnostic apparatus 100 may learn the learning model 900 for determining whether a target nerve is abnormal on the basis of the result of learning the reference honeycomb structure.

For example, the server or the ultrasound diagnostic apparatus 100 may learn a correlation between at least two of the shape and pattern of the honeycomb structure and the structure of the peripheral region on the basis of at least one piece of data on the shape and pattern of the honeycomb structure observed in the normal nerve and the structure of the peripheral region of the honeycomb structure, thereby learning the reference honeycomb structure and generating the learning model 900 for calculating the similarity between the reference honeycomb structure and the target honeycomb structure.

Further, the server or the ultrasound diagnostic apparatus 100 may learn a correlation between at least two of the shape and pattern of the honeycomb structure and the structure of the peripheral region on the basis of at least one piece of data on the shape and pattern of the honeycomb structure observed in the abnormal nerve and the structure of the peripheral region of the honeycomb structure. The server or the ultrasound diagnostic apparatus 100 may precisely learn the reference honeycomb structure and improve the accuracy of the learning model 900 for calculating a similarity between the reference honeycomb structure and the target honeycomb structure by learning the result of learning the honeycomb structure observed in the normal nerve and the result of learning the honeycomb structure observed in the abnormal nerve.

The server or the ultrasound diagnostic apparatus 100 may learn the learning model 900 for determining whether a target nerve is abnormal on the basis of the result of comparison between the similarity between the reference honeycomb structure and the target honeycomb structure and a preset similarity. Here, the preset similarity may be a threshold similarity that becomes a reference for determining the target honeycomb structure as a normal honeycomb structure. As a specific example, the server or the ultrasound diagnostic apparatus 100 may learn and generate the learning model 900 for determining that the target nerve is normal when the similarity between the reference honeycomb structure and the target honeycomb structure is greater than or equal to the preset similarity, and determining that an abnormality is present in the target nerve when the similarity between the reference honeycomb structure and the target honeycomb structure is less than the preset similarity.

In operation 903 of the learning model 900, the server or the ultrasound diagnostic apparatus 100 may acquire a first ultrasound image 921 of the first target nerve as input data of the learning model 900 and determine whether the first target nerve is abnormal. Here, the first ultrasound image 921 of the first target nerve is an ultrasound image including a first nerve region corresponding to the first target nerve.

Specifically, the server or the ultrasound diagnostic apparatus 100 may detect the first nerve region corresponding to the first target nerve from the first ultrasound image 921 and apply a first target honeycomb structure observed in the first nerve region to the learning model 900 to calculate a similarity between the reference honeycomb structure and the first target honeycomb structure. The server or the ultrasound diagnostic apparatus 100 may determine whether the first target nerve is abnormal on the basis of the result of comparison between the calculated similarity and the preset similarity.

For example, when the calculated similarity is greater than or equal to the preset similarity, the server or the ultrasound diagnostic apparatus 100 may determine that the first target nerve is normal. On the other hand, when the calculated similarity is less than the preset similarity, the server or the ultrasound diagnostic apparatus 100 may determine that an abnormality is present in the first target nerve, and detect the abnormal region in which the abnormality is present in the first target nerve. The server or the ultrasound diagnostic apparatus 100 may output the result of determining whether the first target nerve is abnormal through the learning model 900.

For example, referring to block 922, when the first target nerve is determined to be normal, the server or the ultrasound diagnostic apparatus 100 may display information indicating that the first target nerve is normal.

For another example, referring to block 923, when the first target nerve is determined to be abnormal, the server or the ultrasound diagnostic apparatus 100 may display one of information about the abnormal region in the first nerve region corresponding to the first target nerve and basis information about the basis for determining the abnormal region.

Meanwhile, when whether the first target nerve is abnormal is determined for the first ultrasound image 921 in the server, the server may transmit information about the result of determining whether the first target nerve is abnormal to the ultrasound diagnostic apparatus 100.

FIG. 9C is a view for describing honeycomb structures observed in normal nerves and honeycomb structures observed in abnormal nerves, according to one embodiment.

An image 930, an image 940, and an image 950 of FIG. 9C represent honeycomb structures observed in normal nerves. As shown in the image 930, the image 940, and the image 950, in the honeycomb structures observed in the normal nerves, a shape of a unit honeycomb or unit honeycombs constituting the honeycomb structure may be constant, and a pattern according to a brightness value of the unit honeycomb may be constant. In addition, the honeycomb structures observed in the normal nerves may be classified into a honeycomb structure in the image 930, a honeycomb structure in the image 940, and a honeycomb structure in the image 950 depending on the type or location of the nerve. In this case, a structure of a peripheral region of the honeycomb structure may also be different depending on the honeycomb structure.

Meanwhile, an image 960, an image 970, and an image 980 of FIG. 9C represent honeycomb structures observed in abnormal nerves. As shown in the image 960, the image 970, and the image 980, in the honeycomb structures observed in the abnormal nerves, a shape of a unit honeycomb or unit honeycombs constituting the honeycomb structure may not be constant, and a pattern according to a brightness value of the unit honeycomb may not exist.

Figure 10:
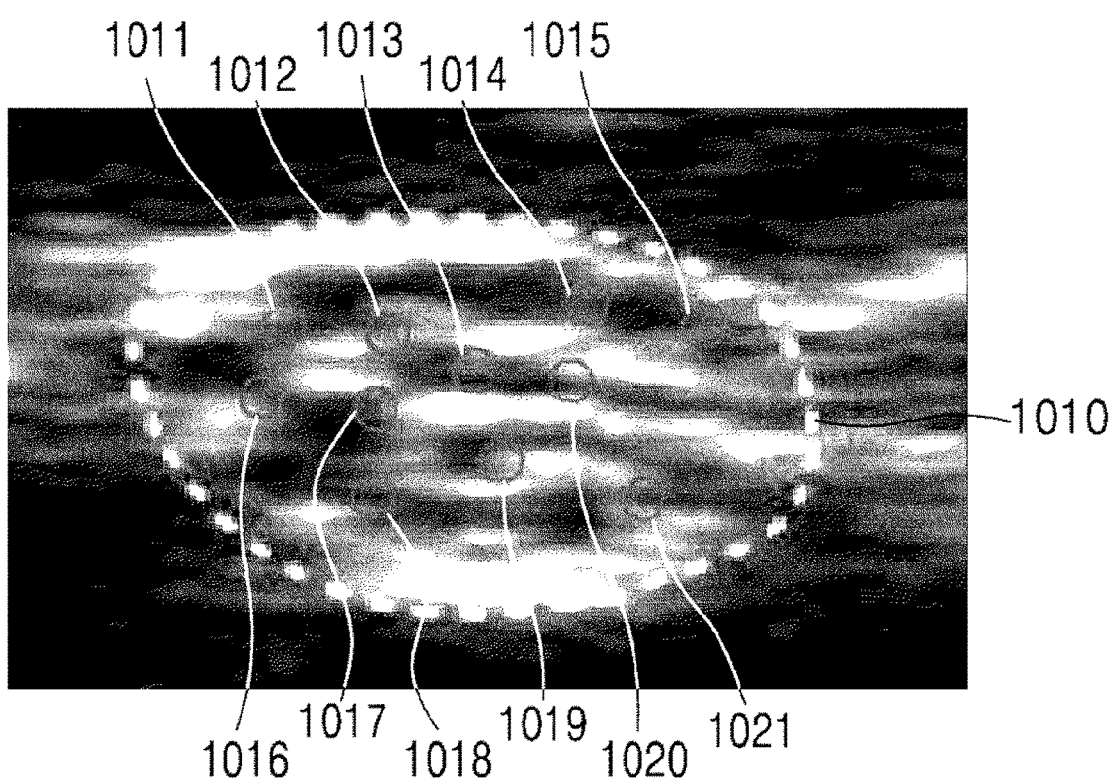
FIG. 10 is a view for describing a process of determining whether a nerve is abnormal on the basis of corner information in an ultrasound image, according to one embodiment.

FIG. 10 is a view for describing a process of determining whether a nerve is abnormal on the basis of corner information in an ultrasound image, according to one embodiment.

The ultrasound diagnostic apparatus 100 may acquire the similarity on the basis of at least one of corner information for each of the reference honeycomb structure in the reference nerve region for the reference nerve and the first target honeycomb structure in the first nerve region for the first target nerve.

As a specific example, the ultrasound diagnostic apparatus 100 may detect corners of reference unit honeycombs, which may be specified as the reference honeycomb structure, on the basis of the reference honeycomb structure. The ultrasound diagnostic apparatus 100 may acquire reference corner information, which includes at least one piece of information about the number, a maximum brightness value, a minimum brightness value, and an average value of brightness values of corner regions corresponding to the reference unit honeycombs.

Further, referring to FIG. 10, the ultrasound diagnostic apparatus 100 may detect corners of unit honeycombs 1011, 1012, 1013, 1014, 1015, 1016, 1017, 1018, 1019, 1020, and 1021 corresponding to the corners of the reference unit honeycombs in the first target honeycomb structure in a first nerve region 1010. The ultrasound diagnostic apparatus 100 may acquire corner information including at least one piece of information about the number, a maximum brightness value, a minimum brightness value, and an average value of brightness values of corner regions corresponding to the unit honeycombs 1011, 1012, 1013, 1014, 1015, 1016, 1017, 1018, 1019, 1020, and 1021.

The ultrasound diagnostic apparatus 100 may compare values of at least one parameter on the basis of the reference corner information and the corner information of the first nerve region 1010, and acquire the similarity on the basis of the comparison result. When the similarity is greater than or equal to the preset similarity, the ultrasound diagnostic apparatus 100 may determine that the first target nerve is normal. On the other hand, when the similarity is less than the preset similarity, the ultrasound diagnostic apparatus 100 may determine that an abnormality is present in the first target nerve. In this case, the ultrasound diagnostic apparatus 100 may detect the first nerve region 1010 corresponding to the first target nerve as the abnormal region and display the first nerve region 1010.

Figure 11A:
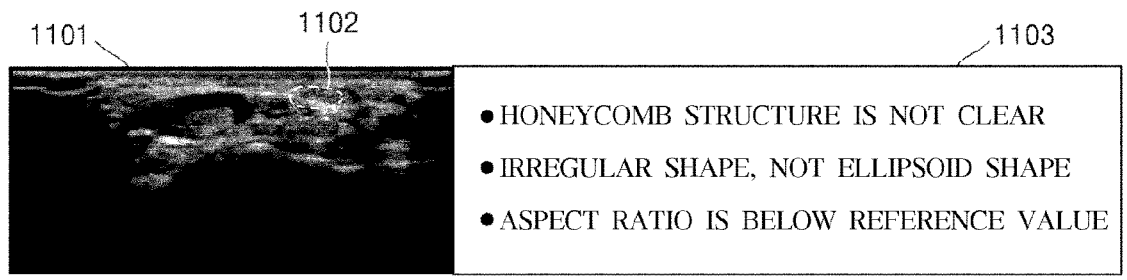
FIG. 11A is an exemplary view of displaying at least one of information about an abnormal region in a nerve and basis information about the basis for determining the abnormal region, in the ultrasound diagnostic apparatus according to one embodiment.

FIG. 11A is an exemplary view of displaying at least one of information about an abnormal region in a nerve and information about the basis for determining the abnormal region, in the ultrasound diagnostic apparatus 100 according to one embodiment.

The ultrasound diagnostic apparatus 100 may display at least one of the information about the abnormal region and basis information about the basis for determining the abnormal region, on the basis of the result of determining whether an abnormal region is present in the first nerve region corresponding to the first target nerve.

Referring to FIG. 11A, the ultrasound diagnostic apparatus 100 may determine whether an abnormality is present in the first target nerve scanned in a first ultrasound image 1101 and detect an abnormal region 1102 in a first nerve region corresponding to the first target nerve. The ultrasound diagnostic apparatus 100 may display the abnormal region 1102 in the first nerve region, which corresponds to the first target nerve, on the first ultrasound image 1101. For example, the abnormal region 1102 may be indicated by a solid line or a dotted line, and may be displayed by applying a predetermined color. In addition, the ultrasound diagnostic apparatus 100 may also display a normal region in the first nerve region, and the normal region and the abnormal region 1102 may be displayed by applying different colors.

Further, the ultrasound diagnostic apparatus 100 may acquire at least one parameter used to determine that an abnormality is present in the first target nerve. For example, the parameter may include at least one of whether a honeycomb structure observed in the nerve region is valid, a similarity of the honeycomb structure, a shape of a nerve region, an aspect ratio of the nerve region, and a size of a cross-sectional area of the nerve region, and the present invention is not limited to the above examples. The ultrasound diagnostic apparatus 100 may acquire information obtained by comparing a value of at least one parameter with a reference value of at least one parameter.

For example, the ultrasound diagnostic apparatus 100 may display at least one of information about the value of at least one parameter, information about a reference value of at least one parameter, and information obtained by comparing the value of at least one parameter with the reference value of at least one parameter.

For example, referring to FIG. 11A, the ultrasound diagnostic apparatus 100 may display basis information 1103 about the basis for determining that the abnormal region 1102 is present in the first nerve region on the basis of a similarity of the honeycomb structure, a shape of the nerve region, and an aspect ratio of the nerve region. Specifically, the ultrasound diagnostic apparatus 100 may display the basis information 1103 such as, "honeycomb structure is not clear," "irregular shape, not an ellipsoid shape," "aspect ratio is below a reference value," or the like.

Figure 11B:
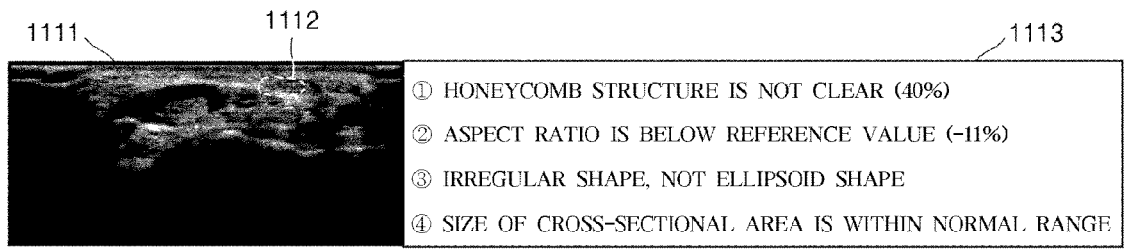
FIG. 11B is an exemplary view of displaying basis information according to a priority of the bases for determining the abnormal region, in the ultrasound diagnostic apparatus according to one embodiment.

FIG. 11B is an exemplary view of displaying basis information according to a priority of the bases for determining the abnormal region, in the ultrasound diagnostic apparatus 100 according to one embodiment.

As shown in FIG. 11B, the ultrasound diagnostic apparatus 100 may determine whether an abnormality is present in the first target nerve scanned from a first ultrasound image 1111, and detect an abnormal region 1112 in a first nerve region corresponding to the first target nerve. The ultrasound diagnostic apparatus 100 may display the abnormal region 1112 in the first nerve region corresponding to the first target nerve on the first ultrasound image 1111.

The ultrasound diagnostic apparatus 100 may display basis information 1113 about the bases for determining that the abnormal region 1112 is present in the first nerve region. In this case, the bases for the determination may be displayed according to a preset priority. Numbers, letters, or symbols may be assigned to each of the bases according to the priority. For example, the preset priority may be determined on the basis of a degree to which values of the parameters, which become a reference for determining whether the first target nerve is abnormal, are out of the preset range.

For example, it may be set that an abnormality is present in the target nerve, in which the target honeycomb structure is observed, when the similarity between the target honeycomb structure and the reference honeycomb structure is less than 70%. As shown in FIG. 11B, the similarity between the first target honeycomb structure and the reference honeycomb structure may be calculated to be 40%. Accordingly, the ultrasound diagnostic apparatus 100 may determine that an abnormality is present in the first target nerve in which the first target honeycomb structure is observed. Meanwhile, when a degree to which the similarity between the first target honeycomb structure and the reference honeycomb structure deviates from the preset similarity is higher than a degree to which a value of a different parameter deviates from the preset range, the similarity between the first target honeycomb structure and the reference honeycomb structure may be the main basis for determining that an abnormality is present in the first target nerve, and the priority may be set as a first priority.

Meanwhile, the ultrasound diagnostic apparatus 100 may display information about a predetermined parameter in the basis information even when a value of the predetermined parameter is in a normal range. As shown in FIG. 11B, the ultrasound diagnostic apparatus 100 may display a phrase indicating information related to the size of the cross-sectional area such as "the size of the cross-sectional area is within a normal range" in the basis information 1113.

Further, the ultrasound diagnostic apparatus 100 may display information obtained by comparing the value of at least one parameter with the reference value of at least one parameter with specific values.

Figure 11C:
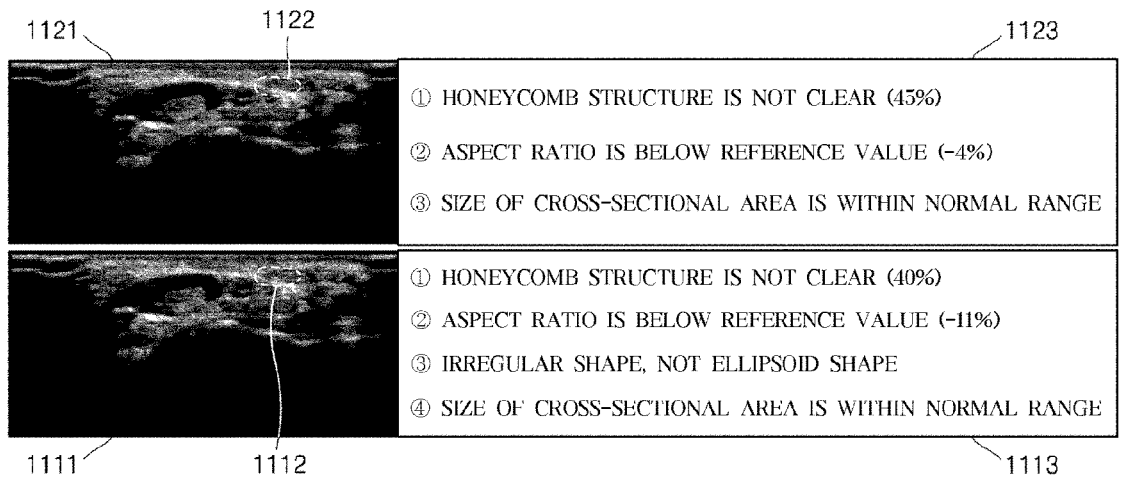
FIG. 11C is an exemplary view of displaying trend information of the abnormal region, in the ultrasound diagnostic apparatus according to one embodiment.

FIG. 11C is an exemplary view of displaying trend information of the abnormal region, in the ultrasound diagnostic apparatus 100 according to one embodiment.

The ultrasound diagnostic apparatus 100 may display an abnormal region 1122 on a first ultrasound image 1121, and may display basis information 1123 about the basis for determining the abnormal region 1122.

The ultrasound diagnostic apparatus 100 may display trend information of the abnormal region for the first target nerve by referring to a previous ultrasound image 1111 that has been acquired before the first ultrasound image 1121 is acquired.

For example, the ultrasound diagnostic apparatus 100 may display the basis information 1123 about the basis for determining the abnormal region 1122 in the first ultrasound image 1121 and the basis information 1113 about the basis for determining the abnormal region 1112 in the previous ultrasound image 1111.

Figure 12:
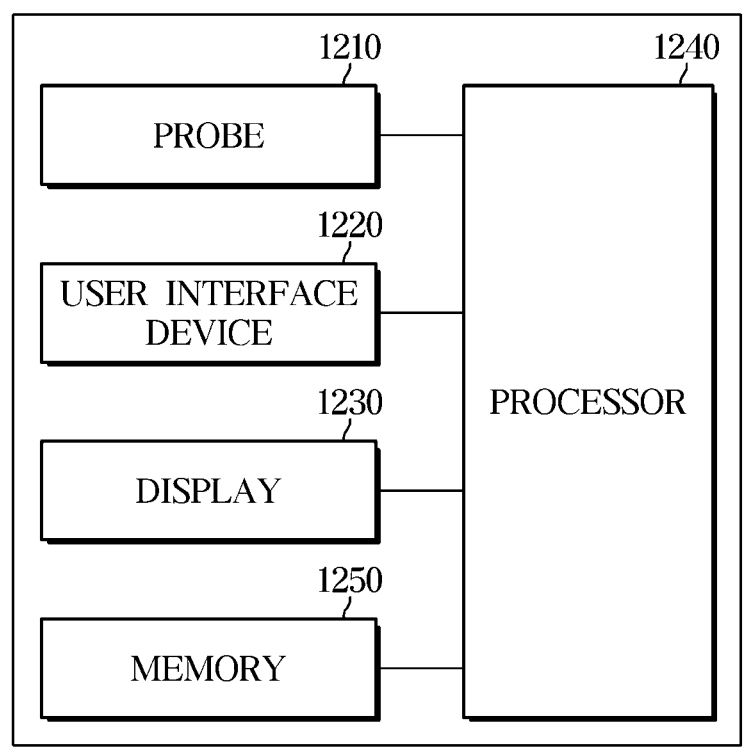
FIG. 12 is a block diagram illustrating a configuration of an ultrasound diagnostic apparatus according to one embodiment.

FIG. 12 is a block diagram illustrating a configuration of an ultrasound diagnostic apparatus according to one embodiment.

As shown in FIG. 12, an ultrasound diagnostic apparatus 100 may include a probe 1210, a user interface device 1220, a display 1230, a memory 1240, and a processor 1240. However, all of the components illustrated in the drawing are not essential components. The ultrasound diagnostic apparatus 100 may be implemented with more or less components than those illustrated in the drawing. Hereinafter, the above components will be described. The ultrasound diagnostic apparatus 100 illustrated in FIG. 12 may be the same as the ultrasound diagnostic apparatus 100 described with reference to FIGS. 1 and 2. In addition, the ultrasound diagnostic apparatus 100 of FIG. 12 may perform the method for operating the ultrasound diagnostic apparatus 100 described with reference to FIGS. 3 to 11.

The probe 1210 may include a plurality of transducer elements to perform conversion between an ultrasound signal and an electrical signal. That is, the probe 1210 may include a transducer array composed of a plurality of transducer elements, and the plurality of transducer elements may be arranged one-dimensionally or two-dimensionally. Each of the plurality of transducer elements may separately generate an ultrasound signal, or the plurality of transducer elements may simultaneously generate ultrasound signals. The ultrasound signal transmitted from each of the transducer elements is reflected by a discontinuous surface of an impedance in an object. Each of the transducer elements may convert a reflected ultrasound signal into an electrical reception signal.

The user interface device 1220 refers to a device for receiving data or signals for controlling the ultrasound diagnostic apparatus 100 from a user. The processor 1240 may control the display 1230 to generate and output a user interface screen for receiving a predetermined command or data from the user.

The display 1230 displays a predetermined screen. Specifically, the display 1230 displays the predetermined screen according to the control of the processor 1240. The display 1230 includes a display panel, and may display an ultrasound image or the like on the display panel.

Meanwhile, the ultrasound diagnostic apparatus 100 may further include the memory 1250. The memory 1250 may store a program for executing the method for operating the ultrasound diagnostic apparatus 100. In addition, the memory 1250 may store code representing the method for operating the ultrasound diagnostic apparatus 100.

The processor 1240 may acquire a first ultrasound image of an object. For example, the probe 1210 in the ultrasound diagnostic apparatus may transmit an ultrasound signal to a region including a first target nerve of the object, and may receive the ultrasound signal reflected from the region including the first target nerve. The processor 1240 may acquire the first ultrasound image for the first target nerve on the basis of the reflected ultrasound signal. The first ultrasound image may be acquired in real time.

The processor 1240 may detect a first nerve region corresponding to the first target nerve in the first ultrasound image.

For example, the processor 1240 may detect the first nerve region corresponding to the first target nerve in the first ultrasound image on the basis of a predetermined automatic detection algorithm or a predetermined automatic segmentation algorithm. The processor 1240 may display the detected first nerve region on the first ultrasound image through the display 1230.

The processor 1240 may determine whether an abnormal region is present in the first nerve region of the first ultrasound image on the basis of a determination standard for determining whether a target nerve is abnormal.

For example, the determination standard may be acquired on the basis of at least one of an anatomical structure in a reference nerve region for a reference nerve, a shape of the reference nerve region, and a size of the reference nerve region. Here, the anatomical structure may be determined on the basis of the shape, size, and relative positional relationship of structures constituting the nerve.

For example, the processor 1240 may determine whether an abnormality is present in the first target nerve on the basis of a honeycomb structure that is an anatomical structure observed in the first target nerve region. Specifically, the processor 1240 may determine whether an abnormal region is present in the first nerve region corresponding to the first target nerve on the basis of a similarity between a reference honeycomb structure in the reference nerve region for the reference nerve and a target honeycomb structure in the target nerve region for the target nerve.

For example, the processor 1240 may acquire a learning model for determining whether a target nerve is abnormal using the similarity between the reference honeycomb structure and the target honeycomb structure. The processor 1240 may apply the first nerve region to the learning model to detect a region in which an abnormal honeycomb structure exists in the first nerve region.

Here, the learning model may be a model in which the reference honeycomb structure is learned on the basis of at least one of a shape and pattern of a honeycomb structure included in a plurality of ultrasound images and a structure of a peripheral region of the honeycomb structure. In addition, the learning model may be a model for determining whether a predetermined target nerve is abnormal when an ultrasound image including a target honeycomb structure in the predetermined target nerve is acquired.

For example, the processor 1240 may acquire the similarity on the basis of a matching rate between the reference honeycomb structure in the reference nerve region of a reference template for the reference nerve and a first target honeycomb structure in the first nerve region. The processor 1240 may determine whether an abnormal region is present in the first nerve region corresponding to the first target nerve on the basis of the acquired similarity.

For example, the processor 1240 may acquire the similarity on the basis of at least one of corner information and feature point information for each of the reference honeycomb structure in the reference nerve region for the reference nerve and the first target honeycomb structure in the first nerve region. The processor 1240 may determine whether an abnormal region is present in the first nerve region corresponding to the first target nerve on the basis of the acquired similarity.

For example, the processor 1240 may determine whether an abnormal region is present in the first nerve region corresponding to the first target nerve on the basis of a second determination standard for determining whether a target nerve is abnormal using a difference between a reference aspect ratio of the reference nerve region for the reference nerve and an aspect ratio of the target nerve region for the target nerve.

For example, the processor 1240 may determine whether an abnormal region is present in the first nerve region corresponding to the first target nerve on the basis of a third determination standard for determining whether a target nerve is abnormal using a difference between a size of a reference cross-sectional area of the reference nerve region for the reference nerve and a size of a cross-sectional area of the target nerve region for the target nerve.

For example, the processor 1240 may acquire a reference value of at least one parameter, which becomes a reference for determining whether a target nerve is abnormal. For example, the parameter may include at least one of whether a honeycomb structure observed in the nerve region is valid, a similarity of the honeycomb structure, a shape of a nerve region, an aspect ratio of the nerve region, and a size of a cross-sectional area of the nerve region, and the present invention is not limited to the above examples. The processor 1240 may determine that an abnormal region is present in the first nerve region when a difference between a value of at least one parameter acquired from the first ultrasound image and the reference value of at least one parameter is out of a preset range.

The processor 1240 may display at least one of information about the abnormal region and basis information about the basis of the abnormal region through the display 1230 on the basis of the result of determining whether an abnormal region is present in the first nerve region.

For example, the basis information about the basis for determining the abnormal region may include information about at least one parameter, which becomes a reference for determining whether the first target nerve is abnormal, and information obtained by comparing the value of at least one parameter and the reference value of at least one parameter.

For example, the display 1230 may display a boundary of the abnormal region on the first ultrasound image. The processor 1240 may display the bases for determining whether an abnormal region is present in the first nerve region according to a preset priority through the display 1230. For example, the preset priority may be determined on the basis of a degree to which values of the parameters, which become a reference for determining whether the first target nerve is abnormal, are out of the preset range.

For example, the display 1230 may display the information about the abnormal region on the first ultrasound image. The processor 1240 may display trend information of the abnormal region for the object through the display 1230 by referring to a previous ultrasound image of the object.

The ultrasound diagnostic apparatus 100 described above may be implemented as hardware components, software components, and/or a combination of hardware components and software components. For example, the apparatuses and components described in the embodiments may be implemented using one or more general-purpose computers or special-purpose computers such as processors, controllers, arithmetic logic units (ALUs), digital signal processors, microcomputers, field programmable arrays (FPAs), programmable logic units (PLUs), microprocessors, or any other apparatuses capable of executing and responding to instructions.

A processing device may execute an operating system (OS) and one or more software applications that are executed on the OS. In addition, the processing device may access, store, operate, process, and generate data in response to the execution of the software.

For convenience of understanding, the processing device may be described as being used singly, but, those of ordinary skill in the art may understand that the processing device may include a plurality of processing elements and/or a plurality of types of processing elements. For example, the processing device may include a plurality of processors or one processor and one controller. In addition, different processing configurations such as parallel processors may also be possible.

The software may include computer programs, code, instructions, or a combination of one or more thereof and may configure the processing device to operate as desired or may command the processing device independently or collectively.

In order to be interpreted by the processing device or to provide commands or data to the processing device, software and/or data may be permanently or temporarily embodied in any type of machine, component, physical apparatus, virtual equipment, computer storage medium or apparatus, or transmitted signal wave. The software may be distributed over a network-coupled computer system to be stored or executed in a distributed manner. The software and data may be stored on one or more computer-readable recording mediums.

The method according to the embodiment may be implemented in the form of program commands executable through various computer means, which may be recorded on a computer-readable recording medium. The computer-readable recording medium may include program commands, data files, and data structures either alone or in combination. The program commands recorded on the computer-readable recording medium may be those that are especially designed and configured for the embodiment, or may be those that are known and available to computer programmers skilled in the art.

Examples of the computer-readable recording mediums may include magnetic recording mediums such as hard disks, floppy disks, and magnetic tapes, optical recording mediums such as compact disk read-only memories (CD-ROMs) and digital versatile disks (DVDs), magneto-optical recording mediums such as floptical disks, and hardware devices such as ROMs, random access memories (RAMs), and flash memories that are especially configured to store and execute program commands.

Examples of the program commands may include machine language code that may be generated by a compiler, and high-level language code that may be executed by a computer using an interpreter.

The hardware device may be configured to operate as one or more software modules in order to perform the operation of the embodiment, and vice versa.

While the embodiments have been described with reference to the drawings, those of ordinary skill in the art may make various changes and modifications therein without departing from the spirit and scope of the inventive concept. For example, the described techniques may be performed in a different order than the described method, and/or the components of the described systems, structures, devices, and circuits may be united or combined in a different form than the described method or may be replaced or substituted by other components or equivalents thereof.

Therefore, other implementations, other embodiments, and equivalents of the following claims are within the scope of the following claims.

The invention claimed is:

1. A method for operating an ultrasound diagnostic apparatus, the method comprising:
acquiring an ultrasound image of an object;
detecting a nerve region corresponding to a target nerve in the ultrasound image;
determining whether an abnormal region is present in the nerve region of the ultrasound image based on a determination standard for determining whether a target nerve is abnormal; and
displaying at least one of information about the abnormal region and basis information about a basis for determining the abnormal region, based on a result of determining whether the abnormal region is present in the nerve region,
wherein the determining whether the abnormal region is present in the nerve region of the ultrasound image is performed using at least one of:
a similarity between a reference honeycomb structure in a reference nerve region for a reference nerve and a target honeycomb structure in a target nerve region for the target nerve,
a difference between a reference aspect ratio of the reference nerve region for the reference nerve and an aspect ratio of the target nerve region for the target nerve, and
a difference between a size of a cross-sectional area of the reference nerve region for the reference nerve and a size of a cross-sectional area of the target nerve region for the target nerve.

2. The method of claim 1, wherein the determining of whether an abnormal region is present in the nerve region based on the determination standard includes:
acquiring a learning model for determining whether the target nerve is abnormal using the similarity between the reference honeycomb structure and the target honeycomb structure; and
detecting a region in which an abnormal honeycomb structure exists in the nerve region by applying the nerve region to the learning model.

3. The method of claim 2, wherein the learning model is a model in which the reference honeycomb structure is learned based on at least one of a shape and pattern of a honeycomb structure included in a plurality of ultrasound images and a structure of a peripheral region of the honeycomb structure, and a model for determining whether a predetermined target nerve is abnormal when an ultrasound image including the target honeycomb structure in the predetermined target nerve is acquired.

4. The method of claim 1, wherein the determining of whether an abnormal region is present in the nerve region based on the determination standard includes one of:
acquiring the similarity based on a matching rate between the reference honeycomb structure in the reference nerve region of a reference template for the reference nerve and a target honeycomb structure in the nerve region; and
acquiring the similarity based on at least one of corner information and feature point information for each of the reference honeycomb structure in the reference nerve region for the reference nerve and the target honeycomb structure in the nerve region.

5. The method of claim 1, wherein the determining of whether an abnormal region is present in the nerve region based on the determination standard for determining whether a target nerve is abnormal includes:
acquiring a reference value of at least one parameter which becomes a reference to determine whether the target nerve is abnormal; and
determining that the abnormal region is present in the nerve region when a difference between a value of the at least one parameter acquired from the ultrasound image and the reference value of the at least one parameter is out of a preset range.

6. The method of claim 1, wherein the basis information about the basis for determining the abnormal region includes information about at least one parameter, which becomes a reference for determining whether the target nerve is abnormal, and information obtained by comparing a value of the at least one parameter and a reference value of the at least one parameter.

7. The method of claim 1, wherein the displaying of at least one of the information about the abnormal region and the basis information about the basis for determining the abnormal region includes at least one of:
displaying a boundary of the abnormal region on the ultrasound image; and
displaying the bases for determining whether the abnormal region is present in the nerve region according to a preset priority.

8. The method of claim 7, wherein the preset priority is determined based on a degree to which values of parameters, which become a reference for determining whether the target nerve is abnormal, are out of a preset range.

9. The method of claim 1, wherein the displaying of at least one of the information about the abnormal region and the basis information about the basis for determining the abnormal region includes:
displaying the information about the abnormal region on the ultrasound image; and
displaying trend information of the abnormal region for the object by referring to a previous ultrasound image for the object.

10. An ultrasound diagnostic apparatus comprising:
a probe configured to transmit an ultrasound signal to an object and receive an ultrasound signal reflected from the object;
a user interface device;
a display;
a processor; and
a memory configured to store instructions executable by the processor,
wherein, the processor is configured to execute the instructions to:
acquire an ultrasound image of the object based on the reflected ultrasound signal;
detect a nerve region corresponding to a target nerve in the ultrasound image;
determine whether an abnormal region is present in the nerve region of the ultrasound image based on a determination standard for determining whether a target nerve is abnormal; and
display at least one of information about the abnormal region and basis information about a basis for determining the abnormal region through the display based on a result of determining whether the abnormal region is present in the nerve region,
wherein the processor is configured to execute the instructions to determine whether the abnormal region is present in the nerve region of the ultrasound image using at least one of:
a similarity between a reference honeycomb structure in a reference nerve region for a reference nerve and a target honeycomb structure in a target nerve region for the target nerve,
a difference between a reference aspect ratio of the reference nerve region for the reference nerve and an aspect ratio of the target nerve region for the target nerve, and
a difference between a size of a cross-sectional area of the reference nerve region for the reference nerve and a size of a cross-sectional area of the target nerve region for the target nerve.

11. A computer program stored in a medium to perform a method in combination with an ultrasound diagnostic apparatus, wherein the method comprises:
acquiring an ultrasound image of an object;
detecting a nerve region corresponding to a target nerve in the ultrasound image;
determining whether an abnormal region is present in the nerve region of the ultrasound image based on a determination standard for determining whether a target nerve is abnormal; and
displaying at least one of information about the abnormal region and basis information about a basis for determining the abnormal region based on a result of determining whether the abnormal region is present in the nerve region,
wherein the determining whether the abnormal region is present in the nerve region of the ultrasound image is performed using at least one of:
a similarity between a reference honeycomb structure in a reference nerve region for a reference nerve and a target honeycomb structure in a target nerve region for the target nerve,
a difference between a reference aspect ratio of the reference nerve region for the reference nerve and an aspect ratio of the target nerve region for the target nerve, and
a difference between a size of a cross-sectional area of the reference nerve region for the reference nerve and a size of a cross-sectional area of the target nerve region for the target nerve.

\* \* \* \* \*